(12) United States Patent
Jones et al.

(10) Patent No.: US 6,306,630 B1
(45) Date of Patent: Oct. 23, 2001

(54) ASPERGILLUS PORPHOBILINOGEN SYNTHASES AND NUCLEIC ACIDS ENCODING SAME

(75) Inventors: Aubrey Jones, Woodland; Joel R. Cherry, Davis, both of CA (US)

(73) Assignee: Novozymes Biotech, Inc., Davis, CA (US)

( * ) Notice: Subject to any disclaimer, the term of this patent is extended or adjusted under 35 U.S.C. 154(b) by 0 days.

(21) Appl. No.: 09/163,674

(22) Filed: Sep. 30, 1998

Related U.S. Application Data

(62) Division of application No. 08/871,268, filed on Jun. 9, 1997, now Pat. No. 5,866,391.
(60) Provisional application No. 60/019,529, filed on Jun. 10, 1996.
(51) Int. Cl.$^7$ .............................. C12N 9/00; C12N 15/63; C12N 5/00; C12N 1/20; C12Q 1/68
(52) U.S. Cl. ........................... 435/183; 435/6; 435/320.1; 435/325; 435/252.3; 435/254.11; 536/23.1; 536/23.2
(58) Field of Search ........................ 435/183, 6, 320.1, 435/325, 252.3, 254.11; 536/23.1, 23.2

(56) References Cited

U.S. PATENT DOCUMENTS 6,100,057 * 8/2000 Elrod et al. ..................... 435/69.1

FOREIGN PATENT DOCUMENTS

WO 93/03185  2/1993  (WO).

OTHER PUBLICATIONS

Myers, et al., Journal of Biological Chemistry, vol. 262, No. 35, pp. 16822–16829 (Dec. 15, 1987).
Mitchell, et al., Journal of Biological Chemistry, vol. 270, No. 41, pp. 24054–24059 (Oct. 13, 1995).
E.K. Jaffe, Journal of Bioenergetics and Biomembranes, vol. 27, No. 2 (Apr. 1995).

* cited by examiner

*Primary Examiner*—Ponnathapu Achutamurthy
*Assistant Examiner*—Peter Tung
(74) *Attorney, Agent, or Firm*—Robert L. Starnes

(57) ABSTRACT

The present invention relates to Aspergillus porphobilinogen synthases and isolated nucleic acid fragments comprising nucleic acid sequences encoding the porphobilinogen synthases as well as nucleic acid constructs, vectors, and recombinant host cells comprising the nucleic acid sequences. The invention also relates to methods of producing the porphobilinogen synthases.

24 Claims, 9 Drawing Sheets

```
CTGGACCAATGGTAACCCTCCGTAATTGCCTTACAGATTTAGCCCAGGGGGGTTATGGTATCCTTGGGTA        70
TTGAGGCCTGGAAATTTTTTTAGCCACCAGTTTACAGCCAGTTTCCGTTTGTAAATATTTCACATCCCCC        140
GACCCTGTCCCAATACAATAATTTTTTCGCTATATATAACGCCCCTAGCGTTGTTTTATGATCCTTAAAT        210
CCTTACTTGTACCTGAAAATTGCAACAAATGTACTGACCTGGATCGCTGGCCATTTATATCATTGCCCTG       280
CGAAGTCGTATTCTGCCAGTGGCACAGGCGCTATTCTCTTTTCTTCCCTCCACCGCGTTTCTATCTTCCA       350
TAGCACCCCACTTGCTTGCCGCTCCTGTCATTATGTCCTTTTCTAATCTCGTCTCTGACCTCGCCTTCAG       420
                                 M  S  F  S  N  L  V  S  D  L  A  F  R
AGATTCTCATGATGACCGAAGTTCTCAGATATCTCAGGTACAATCGCAAGCCACTGCACGATCGTATACA       490
  D  S  H  D  D  R  S  S  Q  I  S  Q  V  Q  S  Q  A  T  A  R  S  Y  T
AGCACAGCTGCCACAAGCGTCAGCATATCTGGCGACATCTCAAGCCAGCTTCATTCCGGTTACAGCCATC       560
  S  T  A  A  T  S  V  S  I  S  G  D  I  S  S  Q  L  H  S  G  Y  S  H
CACTGAGCCGATCATGGCAGGCTGAAAGACAGTTGACTAAAGTCCGCATTTTCTTTTGTATTTACTGAGC       630
  P  L  S  R  S  W  Q  A  E  R  Q  L  T  K
TGCTCTAACCCCGAGATAGGAAATGCTTATTTATCCTCTCTTCATCACCGATAATCCCGATGAGGAGACT       700
     . . . . . . . . . . .  E  M  L  I  Y  P  L  F  I  T  D  N  P  D  E  E  T
CCTATCCCGTCTCTCCCTGGACAGTATCGTCGAGGATTAAACCGTCTAGTTCCTTTCATCAAACCACTTG       770
  P  I  P  S  L  P  G  Q  Y  R  R  G  L  N  R  L  V  P  F  I  K  P  L
CCCACAAGGGGCTACGCTCAGTCATCCTGTTTGGCGTCCCACTACACCCCTCTGCGAAGGATGCACTAGG       840
  A  H  K  G  L  R  S  V  I  L  F  G  V  P  L  H  P  S  A  K  D  A  L  G
TACCGCTGCAGACGATCCATCTGGACCGGTAATTCAAGCTATTCGCTTGCTTAGGTCGCGGTTTCCTCAA       910
  T  A  A  D  D  P  S  G  P  V  I  Q  A  I  R  L  L  R  S  R  F  P  Q
CTTTATATCGTGACAGATGTGTGCCTTTGCGAGTATACTTCGCATGGCCACTGTGGGATACTGCGAGAAG       980
  L  Y  I  V  T  D  V  C  L  C  E  Y  T  S  H  G  H  C  G  I  L  R  E
ATGGGACTCTTGATAATACACAGTCTGTGGATCGGATTTCGGATGTTGCTCTGGCTTATGCTGCCGCCGG       1050
  D  G  T  L  D  N  T  Q  S  V  D  R  I  S  D  V  A  L  A  Y  A  A  A  G
AGCCCATTGTGTCGCTCCGTCTGATATGAATGATGGGCGAGTGCGTGCTATAAAACTGAAGCTTATTGAA       1120
  A  H  C  V  A  P  S  D  M  N  D  G  R  V  R  A  I  K  L  K  L  I  E
GCCGGGATGGCCCACCGTGTCCTACTGATGTCCTACAGCGCCAAATTTAGCGGTTGTTTGTACGGCCCTT       1190
  A  G  M  A  H  R  V  L  L  M  S  Y  S  A  K  F  S  G  C  L  Y  G  P
TCCGTGATGCAGCGGGGTCCTGCCCATCATTCGGGGATCGCAGATGCTACCAGTTACCACCCGGAGGCCG       1260
  F  R  D  A  A  G  S  C  P  S  F  G  D  R  R  C  Y  Q  L  P  P  G  G  R
TGGACTTGCTCGGCGCGCTATACAGAGAGATATAGGCGAAGGGGCAGACATCATAATGGTAAAGCCGGCG       1330
     G  L  A  R  R  A  I  Q  R  D  I  G  E  G  A  D  I  I  M  V  K  P  A
AGCAGCTACCTGGACATTATCAGAGACGCAAAAGAAATTGCCAAAGACATTCCCATTGCTGCTTACCAGG       1400
  S  S  Y  L  D  I  I  R  D  A  K  E  I  A  K  D  I  P  I  A  A  Y  Q
TCAGCGGTGAGTATGCTATGATACATGCTGGTGCCAAGGCGGGCGTATTTGACTTGAAATCCATGGCCTT       1470
  V  S  G  E  Y  A  M  I  H  A  G  A  K  A  G  V  F  D  L  K  S  M  A  F
TGAAAGTACTGAAGGGATTATAAGGGCTGGTGCTGGGATTATAGTAAGCTATTTCGTGCCTGATTTTCTA       1540
  E  S  T  E  G  I  I  R  A  G  A  G  I  I  V  S  Y  F  V  P  D  F  L
GATTGGCTTTCGAAATGATTTAGCTAGATGGAGCGTGATGAAAGCATCCACCAGATAAATAGCAGTGACG       1610
  D  W  L  S  K
ATCGCGTTTGAATCATACCTATTGGAGTAGAAGTCTCGGTATCTCGTTGGGGATTCTCTAGGTTGCTTAT       1680
TTAACGTAATGCCACGCCATGTGTTATATATTGCCTAAATACTTTTATAAAAGATACACCAAGCTGATGG       1750
TGCCAAGTGACCACTTCTAATAAATACAATTATACCAATTCCTCCGAAATATGCGGG        1807
```

FIG. 2

```
  1   MSQSF----------------------- B. subtilis hemB
  1   -TDLI----------------------- E. coli hemB
  1   M---------------QPQ--------- human hemB
  1   ---------------HTFVDLKSPFTLSNY pea hemB
  1   M---------------HHQ--------- rat hemB
  1   MMASTFNIPCNAGTIKNFNNSQRNLGFSSN spinach hemB
  1   M---------------HTAEFLE----- yeast hemB
  1   M---------------SFSNLVSDLAFRD- Ao hemB 6   ----------------------------- B. subtilis hemB
  5   ----------------------------- E. coli hemB
  5   ----------------------------- human hemB
 16   LSFSSSKRR--------QPPSLFTVRASDS pea hemB
  5   ----------------------------- rat hemB
 31   LGINFAKTRFSNCGDSGRIPSQLVVRASER spinach hemB
  9   ----------------------------- yeast hemB
 15   ------------------------SHDDR Ao hemB 6   ----------------------------- B. subtilis hemB
  5   ----------------------------- E. coli hemB
  5   ----------------------------- human hemB
 38   ---------------DFEAAVVAGKVPEAPP pea hemB
  5   ----------------------------- rat hemB
 61   RDNLTQQKTGLSIEECEAAVVAGNAPSAPP spinach hemB
  9   ----------------------------- yeast hemB
 20   SSQISQVQSQATARSYTST---------- Ao hemB 6   --------------------NRHRRLRTSK B. subtilis hemB
  5   --------------------QRPRRLRKSP E. coli hemB
  5   --------------SVLHSGYFHPLLRAWQ human hemB
 54   VPPTPASPAGTPVVPSLPIQRPRRNRRSP pea hemB
  5   --------------SVLHSGYFHPLLRAWQ rat hemB
 91   VPPTPKAPSGTPSVSPLSLGRPRRNRTSP spinach hemB
  9   --------TEPTEISVLAGYNHPLLRQWQ yeast hemB
 39   --AATSVSISGDISQLHSGYSHPLSRSWQ Ao hemB 16   AMREMVKETRLHPSDFIYPIFVVEGLEGKK B. subtilis hemB
 15   ALPRMFEETTLSLNDLVLPIFVEEIDDYK E. coli hemB
 21   T-----ATTTLNASNLIYPIFVTDVPDDIQ human hemB
 84   ALRSAFQETTLSPANFVYPLFIHEGEED-T pea hemB
 21   T-----TPSTVSATNLIYPIFVTDVPDDVQ rat hemB
121   VFRAAFQETTLSPANVVYPLFIHEGEED-T spinach hemB
 32   ------SERQLTKNMLIFPLFISDNPDDFT yeast hemB
 67   ------AERQLTKEMLIYPLFITDNPDEET Ao hemB 46   AVPSMPDVHHVSLDL-LKDEVAELVKLGIQ B. subtilis hemB
 45   AVEAMPGVMRIPEKH-LAREIERIANAGIR E. coli hemB
 46   PITSLPGVARYGVKR-LEEMLRPLVEEGLR human hemB
113   PIGAMPGCYRLGWRHGLLEEVAKARDVGVN pea hemB
 46   PIASLPGVARYGVNQ-LEEMLRPLVEAGLR rat hemB
150   PIGAMPGCYRLGWRHGLVEEVAKARDVVVN spinach hemB
 56   EIDSLPNINRIGVNR-LKDYLKPLVAKGLR yeast hemB
 91   PIPSLPGQYRRGLNR-LVPFIKPLAHKGLR Ao hemB
```

FIG. 3A

```
 75 SVIVFG--IPEE-KDDCGTQAYHDHGIVQK    B. subtilis hemB
 74 SVMTFG--ISHH-TDETGERAWREDGLVAR    E. coli hemB
 75 CVLIFGVP-SRVPKDERGSAADSEESPAIE    human hemB
143 SVVLFP-KIPDALKTPTGDEAYNEDGLVPR    pea hemB
 75 CVLIFGVP-SRVPKDEQGSAADSEDSPTIE    rat hemB
180 SIVVFP-K-PDALKSPTGDEAYNENGLVPR    spinach hemB
 85 SVILFGVPLIPGTKDPVGTAADDPAGPVIQ    yeast hemB
120 SVILFGVPLHPSAKDALGTAADDPSGPVIQ    Ao hemB 102 AITEIKEHFPEMVVADTCLCEYTDHGHCG    B. subtilis hemB
101 MSRICKQTVPEMIVMSDTCFCEYTSHGHCG    E. coli hemB
104 AIHLLRKTFPNLLVACDVCLCPYTSHGHCG    human hemB
172 SIRLLKDKYPDLIIYTDVALDPYSSDGHDG    pea hemB
104 AVRLLRKTFPTLLVACDVCLCPYTSHGHCG    rat hemB
208 TIRMLKDKFPDLIIYTDVALDPYYYDGHDG    spinach hemB
115 GIKFIREYFPELYIICDVCLCEYTSHGHCG    yeast hemB
150 AIRLLRSRFPQLYIVTDVCLCEYTSHGHCG    Ao hemB 132 LVKDGV-ILNDESLELLAQTAVSQAKAGAD    B. subtilis hemB
131 VLCEHG-VDNDATLENLGKQAVVAAAGAD    E. coli hemB
134 LLSENGAFRAEESRQRLAEVALAYAKAGCQ    human hemB
202 IVREDGVIMNDETVHQLCKQAVAQARAGAD    pea hemB
134 LLSENGAFLAEESRQRLAEVALAYAKAGCQ    rat hemB
238 IVTQHGVIMNDETVHQLCKQAVAQARAGAD    spinach hemB
145 VLYDDGTINRERSVSRLAAVAVNYAKAGAH    yeast hemB
180 ILREDGTLDNTQSVDRISDVALAYAAAGAH    Ao hemB 161 IIAPSNMMDGFVTVIREALDKEGFVN-IPI    B. subtilis hemB
160 FIAPSAAMDGQVQAIRQALDAAGFKD-TAI    E. coli hemB
164 VVAPSDMMDGRVEAIKEALMAHGLGNRVSV    human hemB
232 VVSPSDMMDGRVGAMRVALDAEGFQH-VSI    pea hemB
164 VVAPSDMMDGRVEAIKAALLKHGLGNRVSV    rat hemB
268 VVSPSDMMDGRVGAIRAALDAEGYSN-VSI    spinach hemB
175 CVAPSDMIDGRIRDIKRGLINANLAHKTFV    yeast hemB
210 CVAPSDMNDGRVRAIKLKLIEAGMAHRVLL    Ao hemB 190 MSYAVKYSSEFYGPFRDAANSTPQFGDRKT    B. subtilis hemB
189 MSYSTKFASSFYGPFREAAGSALK-GDRKS    E. coli hemB
194 MSYSAKFASCFYGPFRDAAKSSPAFGDRRC    human hemB
261 MSYTAKYASSFYGPFREALDSNPRFGDKKT    pea hemB
194 MSYSAKFASCFYGPFRDAAQSSPAFGDRRC    rat hemB
297 MSYTAKYASSFY-----------PRFGDKKT    spinach hemB
205 LSYAKFSGNLYGPFRDAACSAPSNGDRKC    yeast hemB
240 MSYAKFSGCLYGPFRDAAGSCPSFGDRRC    Ao hemB 220 YQMDPANRMEALREAQSDVEEGADFLIVKP    B. subtilis hemB
218 YQMNPMNRAEGIAEYLLDEAQGADCLMVKP    E. coli hemB
224 YQLPPGARGLALRAVDRDVREGADMLVKP    human hemB
291 YQMNPANYREALTEMREDESEGADILLVKP   pea hemB
224 YQLPPGARGLALRAVARDIQEGADILMVKP   rat hemB
317 YQMNPANYREALIETQEDESEGADILLVKP   spinach hemB
235 YQLPPAGRGLARRALERDMSEGADGIIVKP   yeast hemB
270 YQLPPGGRGLARRAIQRDIGEGADIIMVKP   Ao hemB
```

FIG. 3B

```
250 S L S Y M D I M R D V K N E F - T L P L V A Y N V S G E Y S   B. subtilis hemB
248 A G A Y L D I V R E L R E R T - E L P I G A Y Q V S G E Y A   E. coli hemB
254 G M P Y L D I V R E V K D H P D L P L A V Y H V S G E F A     human hemB
321 G L P Y L D I I R L L R D N S - P L P I A A Y Q V S G E Y S   pea hemB
254 G L P Y L D M V Q E V K D H P E L P L A V Y Q V S G E F A     rat hemB
347 G L P Y L D I I R L L R D N S - D L P I A A Y Q V S G E Y S   spinach hemB
265 S T F Y L D I M R D A S E I C K D L P I C A Y H V S D E Y A   yeast hemB
300 A S S Y L D I I R D A K E I A K D I P I A A Y Q V S G E Y A   Ao hemB 279 M V K A A A Q N G W I K E K E I V L E I L T S M K R A G A D   B. subtilis hemB
277 M I K F A A L A G A I D E E K V V L E S L G S I K R A G A D   E. coli hemB
284 M L W H G A Q A G A F D L K A A V L E A M T A F R R A G A D   human hemB
350 M I K A G G A L K M I D E E K V M M E S L L C L R R A G A D   pea hemB
284 M L W H G A K A G A F D L R T A V L E S M T A F R R A G A D   rat hemB
376 M I K A G G V L K M I D E E K V M L E S L L C L R R A G A D   spinach hemB
295 M L H A A E K G V V D L K T I A F E S H Q G F L R A G A R     yeast hemB
330 M I H A G A K A G V F D L K S M A F E S T E G I I R A G A G   Ao hemB 309 L I I T Y H A K D - A A K W L - - - A E                       B. subtilis hemB
307 L I F S Y F A L D L A E K K I - - - L R                       E. coli hemB
314 I I I T Y Y T P Q L L - Q W L - K E E                         human hemB
380 I I L T Y F A L Q - A A R T L C G E K R                       pea hemB
314 I I I T Y F A P Q L L - K W L - K E E                         rat hemB
406 I I L T Y F A L Q - A A R C L C G E K R                       spinach hemB
325 L I I T Y L A P E F L - D W L - D E E N                       yeast hemB
360 I I V S Y F V P D F L - D W L - S - - K                       Ao hemB
```

FIG. 3C

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
        (A) LENGTH: 1807 base pairs
        (B) TYPE: nucleic acid
        (C) STRANDEDNESS: single
        (D) TOPOLOGY: linear (xi) SEQUENCE DESCRIPTION: SEQ ID NO:1:

```
CTGGACCAAT GGTAACCCTC CGTAATTGCC TTACAGATTT AGCCCAGGGG GGTTATGGTA      60

TCCTTGGGTA TTGAGGCCTG GAAATTTTTT TAGCCACCAG TTTACAGCCA GTTTCCGTTT     120

GTAAATATTT CACATCCCCC GACCCTGTCC CAATACAATA ATTTTTTCGC TATATATAAC     180

GCCCCTAGCG TTGTTTTATG ATCCTTAAAT CCTTACTTGT ACCTGAAAAT TGCAACAAAT     240

GTACTGACCT GGATCGCTGG CCATTTATAT CATTGCCCTG CGAAGTCGTA TTCTGCCAGT     300

GGCACAGGCG CTATTCTCTT TTCTTCCCTC CACCGCGTTT CTATCTTCCA TAGCACCCCA     360

CTTGCTTGCC GCTCCTGTCA TTATGTCCTT TTCTAATCTC GTCTCTGACC TCGCCTTCAG     420

AGATTCTCAT GATGACCGAA GTTCTCAGAT ATCTCAGGTA CAATCGCAAG CCACTGCACG     480

ATCGTATACA AGCACAGCTG CCACAAGCGT CAGCATATCT GGCGACATCT CAAGCCAGCT     540

TCATTCCGGT TACAGCCATC CACTGAGCCG ATCATGGCAG GCTGAAAGAC AGTTGACTAA     600

AGTCCGCATT TTCTTTTGTA TTTACTGAGC TGCTCTAACC CCGAGATAGG AAATGCTTAT     660
```

```
TTATCCTCTC TTCATCACCG ATAATCCCGA TGAGGAGACT CCTATCCCGT CTCTCCCTGG      720

ACAGTATCGT CGAGGATTAA ACCGTCTAGT TCCTTTCATC AAACCACTTG CCCACAAGGG      780

GCTACGCTCA GTCATCCTGT TTGGCGTCCC ACTACACCCC TCTGCGAAGG ATGCACTAGG      840

TACCGCTGCA GACGATCCAT CTGGACCGGT AATTCAAGCT ATTCGCTTGC TTAGGTCGCG      900

GTTTCCTCAA CTTTATATCG TGACAGATGT GTGCCTTTGC GAGTATACTT CGCATGGCCA      960

CTGTGGATA CTGCGAGAAG ATGGGACTCT TGATAATACA CAGTCTGTGG ATCGGATTTC      1020

GGATGTTGCT CTGGCTTATG CTGCCGCCGG AGCCCATTGT GTCGCTCCGT CTGATATGAA      1080

TGATGGGCGA GTGCGTGCTA TAAAACTGAA GCTTATTGAA GCCGGGATGG CCCACCGTGT      1140

CCTACTGATG TCCTACAGCG CCAAATTTAG CGGTTGTTTG TACGGCCCTT TCCGTGATGC      1200

AGCGGGGTCC TGCCCATCAT TCGGGGATCG CAGATGCTAC CAGTTACCAC CCGGAGGCCG      1260

TGGACTTGCT CGGCGCGCTA TACAGAGAGA TATAGGCGAA GGGGCAGACA TCATAATGGT      1320

AAAGCCGGCG AGCAGCTACC TGGACATTAT CAGAGACGCA AAAGAAATTG CCAAAGACAT      1380

TCCCATTGCT GCTTACCAGG TCAGCGGTGA GTATGCTATG ATACATGCTG GTGCCAAGGC      1440

GGGCGTATTT GACTTGAAAT CCATGGCCTT TGAAAGTACT GAAGGGATTA TAAGGGCTGG      1500

TGCTGGGATT ATAGTAAGCT ATTTCGTGCC TGATTTTCTA GATTGGCTTT CGAAATGATT      1560

TAGCTAGATG GAGCGTGATG AAAGCATCCA CCAGATAAAT AGCAGTGACG ATCGCGTTTG      1620

AATCATACCT ATTGGAGTAG AAGTCTCGGT ATCTCGTTGG GGATTCTCTA GGTTGCTTAT      1680

TTAACGTAAT GCCACGCCAT GTGTTATATA TTGCCTAAAT ACTTTTATAA AGATACACC      1740

AAGCTGATGG TGCCAAGTGA CCACTTCTAA TAAATACAAT TATACCAATT CCTCCGAAAT      1800

ATGCGGG                                                               1807

(2) INFORMATION FOR SEQ ID NO:2:

(i) SEQUENCE CHARACTERISTICS:
        (A) LENGTH: 375 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

Met Ser Phe Ser Asn Leu Val Ser Asp Leu Ala Phe Arg Asp Ser His
 1               5                  10                  15

Asp Asp Arg Ser Ser Gln Ile Ser Gln Val Gln Ser Gln Ala Thr Ala
            20                  25                  30

Arg Ser Tyr Thr Ser Thr Ala Ala Thr Ser Val Ser Ile Ser Gly Asp
        35                  40                  45

Ile Ser Ser Gln Leu His Ser Gly Tyr Ser His Pro Leu Ser Arg Ser
50                  55                  60

Trp Gln Ala Glu Arg Gln Leu Thr Lys Glu Met Leu Ile Tyr Pro Leu
65                  70                  75                  80

Phe Ile Thr Asp Asn Pro Asp Glu Glu Thr Pro Ile Pro Ser Leu Pro
                85                  90                  95

Gly Gln Tyr Arg Arg Gly Leu Asn Arg Leu Val Pro Phe Ile Lys Pro
            100                 105                 110

Leu Ala His Lys Gly Leu Arg Ser Val Ile Leu Phe Gly Val Pro Leu
        115                 120                 125
```

```
His Pro Ser Ala Lys Asp Ala Leu Gly Thr Ala Ala Asp Asp Pro Ser
    130                 135                 140

Gly Pro Val Ile Gln Ala Ile Arg Leu Leu Arg Ser Arg Phe Pro Gln
145                 150                 155                 160

Leu Tyr Ile Val Thr Asp Val Cys Leu Cys Glu Tyr Thr Ser His Gly
                165                 170                 175

His Cys Gly Ile Leu Arg Glu Asp Gly Thr Leu Asp Asn Thr Gln Ser
                180                 185                 190

Val Asp Arg Ile Ser Asp Val Ala Leu Ala Tyr Ala Ala Ala Gly Ala
                195                 200                 205

His Cys Val Ala Pro Ser Asp Met Asn Asp Gly Arg Val Arg Ala Ile
            210                 215                 220

Lys Leu Lys Leu Ile Glu Ala Gly Met Ala His Arg Val Leu Leu Met
225                 230                 235                 240

Ser Tyr Ser Ala Lys Phe Ser Gly Cys Leu Tyr Gly Pro Phe Arg Asp
                245                 250                 255

Ala Ala Gly Ser Cys Pro Ser Phe Gly Asp Arg Arg Cys Tyr Gln Leu
                260                 265                 270

Pro Pro Gly Gly Arg Gly Leu Ala Arg Arg Ala Ile Gln Arg Asp Ile
                275                 280                 285

Gly Glu Gly Ala Asp Ile Ile Met Val Lys Pro Ala Ser Ser Tyr Leu
                290                 295                 300

Asp Ile Ile Arg Asp Ala Lys Glu Ile Lys Asp Ile Pro Ile Ala
305                 310                 315                 320

Ala Tyr Gln Val Ser Gly Glu Tyr Ala Met Ile His Ala Gly Ala Lys
                325                 330                 335

Ala Gly Val Phe Asp Leu Lys Ser Met Ala Phe Glu Ser Thr Glu Gly
                340                 345                 350

Ile Ile Arg Ala Gly Ala Gly Ile Ile Val Ser Tyr Phe Val Pro Asp
                355                 360                 365

Phe Leu Asp Trp Leu Ser Lys
    370                 375

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:3:

GTNGCNCCNW SNGAYATGAT GGA                                      23

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:4:

GCRTCNCGTR AANCCRTA                                            18

(2) INFORMATION FOR SEQ ID NO:5:

(i) SEQUENCE CHARACTERISTICS:
```

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:5:

GTGGCTCCGA GTGATAT                                                          17

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:6:

GCATCGCGAA AAGGACCG                                                         18

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:7:

GCATATTTAA ATGATGTCCT TTCTAATCT CGT                                         33

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:8:

ATATTAATTA ATCCATCTAG CTAAATCATT                                            30

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:9:

GCGCGAATTC GTNGGNATNG GNATNAAYCA YGG                                        33

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:10:

GCGGATCCGG NGGRCARTTN GACAT                                                 25

(2) INFORMATION FOR SEQ ID NO:11:

(i) SEQUENCE CHARACTERISTICS:
        (A) LENGTH: 28 base pairs (B) TYPE: nucleic acid
            (C) STRANDEDNESS: single
            (D) TOPOLOGY: linear (xi) SEQUENCE DESCRIPTION: SEQ ID NO:11:

GCGAATTCAC NCCNCARGTN TTYGAYAC                                              28

(2) INFORMATION FOR SEQ ID NO:12:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO:12:

GCGGATCCRA AYTCNCCNGG RAANGG                                                26

(2) INFORMATION FOR SEQ ID NO:13:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:13:

GCGCGAATTC TGGCARTCNA C                                                     21

(2) INFORMATION FOR SEQ ID NO:14:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:14:

GCGCGAATTC TGGCARAGNA TG                                                    22

(2) INFORMATION FOR SEQ ID NO:15:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:15:

GGATCCGACA TYTTNGCCAT NGC                                                   23

(2) INFORMATION FOR SEQ ID NO:16:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:16:

GTYTCRATRT AGAAYTG                                                          17

(2) INFORMATION FOR SEQ ID NO:17:

(i) SEQUENCE CHARACTERISTICS:

(A) LENGTH: 342 amino acids
(B) TYPE: amino acid
(C) STRANDEDNESS: single
(D) TOPOLOGY: linear (ii) MOLECULE TYPE: None (xi) SEQUENCE DESCRIPTION: SEQ ID NO:17:

```
Met His Thr Ala Glu Phe Leu Glu Thr Glu Pro Thr Glu Ile Ser Ser
1               5                   10                  15

Val Leu Ala Gly Gly Tyr Asn His Pro Leu Leu Arg Gln Trp Gln Ser
                20                  25                  30

Glu Arg Gln Leu Thr Lys Asn Met Leu Ile Phe Pro Leu Phe Ile Ser
            35                  40                  45

Asp Asn Pro Asp Asp Phe Thr Glu Ile Asp Ser Leu Pro Asn Ile Asn
        50                  55                  60

Arg Ile Gly Val Asn Arg Leu Lys Asp Tyr Leu Lys Pro Leu Val Ala
65                  70                  75                  80

Lys Gly Leu Arg Ser Val Ile Leu Phe Gly Val Pro Leu Ile Pro Gly
                85                  90                  95

Thr Lys Asp Pro Val Gly Thr Ala Ala Asp Asp Pro Ala Gly Pro Val
                100                 105                 110

Ile Gln Gly Ile Lys Phe Ile Arg Glu Tyr Phe Pro Glu Leu Tyr Ile
            115                 120                 125

Ile Cys Asp Val Cys Leu Cys Glu Tyr Thr Ser His Gly His Cys Gly
        130                 135                 140

Val Leu Tyr Asp Asp Gly Thr Ile Asn Arg Glu Arg Ser Val Ser Arg
145                 150                 155                 160

Leu Ala Ala Val Ala Val Asn Tyr Ala Lys Ala Gly Ala His Cys Val
                165                 170                 175

Ala Pro Ser Asp Met Ile Asp Gly Arg Ile Arg Asp Ile Lys Arg Gly
                180                 185                 190

Leu Ile Asn Ala Asn Leu Ala His Lys Thr Phe Val Leu Ser Tyr Ala
            195                 200                 205

Ala Lys Phe Ser Gly Asn Leu Tyr Gly Pro Phe Arg Asp Ala Ala Cys
        210                 215                 220

Ser Ala Pro Ser Asn Gly Asp Arg Lys Cys Tyr Gln Leu Pro Pro Ala
225                 230                 235                 240

Gly Arg Gly Leu Ala Arg Arg Ala Leu Glu Arg Asp Met Ser Glu Gly
                245                 250                 255

Ala Asp Gly Ile Ile Val Lys Pro Ser Thr Phe Tyr Leu Asp Ile Met
                260                 265                 270

Arg Asp Ala Ser Glu Ile Cys Lys Asp Leu Pro Ile Cys Ala Tyr His
            275                 280                 285

Val Ser Asp Glu Tyr Ala Met Leu His Ala Ala Ala Glu Lys Gly Val
            290                 295                 300

Val Asp Leu Lys Thr Ile Ala Phe Glu Ser His Gln Gly Phe Leu Arg
305                 310                 315                 320

Ala Gly Ala Arg Leu Ile Ile Thr Tyr Leu Ala Pro Glu Phe Leu Asp
                325                 330                 335

Trp Leu Asp Glu Glu Asn
            340
```

(2) INFORMATION FOR SEQ ID NO:18:

(i) SEQUENCE CHARACTERISTICS:

(A) LENGTH: 330 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:18:

Met Gln Pro Gln Ser Val Leu His Ser Gly Tyr Phe His Pro Leu Leu
 1               5                  10                  15

Arg Ala Trp Gln Thr Ala Thr Thr Thr Leu Asn Ala Ser Asn Leu Ile
            20                  25                  30

Tyr Pro Ile Phe Val Thr Asp Val Pro Asp Asp Ile Gln Pro Ile Thr
        35                  40                  45

Ser Leu Pro Gly Val Ala Arg Tyr Gly Val Lys Arg Leu Glu Glu Met
 50                  55                  60

Leu Arg Pro Leu Val Glu Glu Gly Leu Arg Cys Val Leu Ile Phe Gly
 65                  70                  75                  80

Val Pro Ser Arg Val Pro Lys Asp Glu Arg Gly Ser Ala Ala Asp Ser
                85                  90                  95

Glu Glu Ser Pro Ala Ile Glu Ala Ile His Leu Leu Arg Lys Thr Phe
            100                 105                 110

Pro Asn Leu Leu Val Ala Cys Asp Val Cys Leu Cys Pro Tyr Thr Ser
            115                 120                 125

His Gly His Cys Gly Leu Leu Ser Glu Asn Gly Ala Phe Arg Ala Glu
        130                 135                 140

Glu Ser Arg Gln Arg Leu Ala Glu Val Ala Leu Ala Tyr Ala Lys Ala
145                 150                 155                 160

Gly Cys Gln Val Val Ala Pro Ser Asp Met Met Asp Gly Arg Val Glu
                165                 170                 175

Ala Ile Lys Glu Ala Leu Met Ala His Gly Leu Gly Asn Arg Val Ser
            180                 185                 190

Val Met Ser Tyr Ser Ala Lys Phe Ala Ser Cys Phe Tyr Gly Pro Phe
        195                 200                 205

Arg Asp Ala Ala Lys Ser Ser Pro Ala Phe Gly Asp Arg Arg Cys Tyr
    210                 215                 220

Gln Leu Pro Pro Gly Ala Arg Gly Leu Ala Leu Arg Ala Val Asp Arg
225                 230                 235                 240

Asp Val Arg Glu Gly Ala Asp Met Leu Met Val Lys Pro Gly Met Pro
                245                 250                 255

Tyr Leu Asp Ile Val Arg Glu Val Lys Asp Lys His Pro Asp Leu Pro
            260                 265                 270

Leu Ala Val Tyr His Val Ser Gly Glu Phe Ala Met Leu Trp His Gly
        275                 280                 285

Ala Gln Ala Gly Ala Phe Asp Leu Lys Ala Ala Val Leu Glu Ala Met
    290                 295                 300

Thr Ala Phe Arg Arg Ala Gly Ala Asp Ile Ile Ile Thr Tyr Tyr Thr
305                 310                 315                 320

Pro Gln Leu Leu Gln Trp Leu Lys Glu Glu
                325                 330

(2) INFORMATION FOR SEQ ID NO:19:

(i) SEQUENCE CHARACTERISTICS:
        (A) LENGTH: 330 amino acids
        (B) TYPE: amino acid
        (C) STRANDEDNESS: single (D) TOPOLOGY: linear (ii) MOLECULE TYPE: None (xi) SEQUENCE DESCRIPTION: SEQ ID NO:19:

```
Met His His Gln Ser Val Leu His Ser Gly Tyr Phe His Pro Leu Leu
1               5                   10                  15

Arg Ala Trp Gln Thr Thr Pro Ser Thr Val Ser Ala Thr Asn Leu Ile
                20                  25                  30

Tyr Pro Ile Phe Val Thr Asp Val Pro Asp Asp Val Gln Pro Ile Ala
            35                  40                  45

Ser Leu Pro Gly Val Ala Arg Tyr Gly Val Asn Gln Leu Glu Glu Met
    50                  55                  60

Leu Arg Pro Leu Val Glu Ala Gly Leu Arg Cys Val Leu Ile Phe Gly
65                  70                  75                  80

Val Pro Ser Arg Val Pro Lys Asp Glu Gln Gly Ser Ala Ala Asp Ser
                85                  90                  95

Glu Asp Ser Pro Thr Ile Glu Ala Val Arg Leu Leu Arg Lys Thr Phe
                100                 105                 110

Pro Thr Leu Leu Val Ala Cys Asp Val Cys Leu Cys Pro Tyr Thr Ser
            115                 120                 125

His Gly His Cys Gly Leu Leu Ser Glu Asn Gly Ala Phe Leu Ala Glu
    130                 135                 140

Glu Ser Arg Gln Arg Leu Ala Glu Val Ala Leu Ala Tyr Ala Lys Ala
145                 150                 155                 160

Gly Cys Gln Val Val Ala Pro Ser Asp Met Met Asp Gly Arg Val Glu
                165                 170                 175

Ala Ile Lys Ala Ala Leu Leu Lys His Gly Leu Gly Asn Arg Val Ser
                180                 185                 190

Val Met Ser Tyr Ser Ala Lys Phe Ala Ser Cys Phe Tyr Gly Pro Phe
            195                 200                 205

Arg Asp Ala Ala Gln Ser Ser Pro Ala Phe Gly Asp Arg Arg Cys Tyr
    210                 215                 220

Gln Leu Pro Pro Gly Ala Arg Gly Leu Ala Leu Arg Ala Val Ala Arg
225                 230                 235                 240

Asp Ile Gln Glu Gly Ala Asp Ile Leu Met Val Lys Pro Gly Leu Pro
                245                 250                 255

Tyr Leu Asp Met Val Gln Glu Val Lys Asp Lys His Pro Glu Leu Pro
            260                 265                 270

Leu Ala Val Tyr Gln Val Ser Gly Glu Phe Ala Met Leu Trp His Gly
    275                 280                 285

Ala Lys Ala Gly Ala Phe Asp Leu Arg Thr Ala Val Leu Glu Ser Met
290                 295                 300

Thr Ala Phe Arg Arg Ala Gly Ala Asp Ile Ile Ile Thr Tyr Phe Ala
305                 310                 315                 320

Pro Gln Leu Leu Lys Trp Leu Lys Glu Glu
                325                 330
```

(2) INFORMATION FOR SEQ ID NO:20:

(i) SEQUENCE CHARACTERISTICS:
(A) LENGTH: 323 amino acids
(B) TYPE: amino acid
(C) STRANDEDNESS: single
(D) TOPOLOGY: linear (ii) MOLECULE TYPE: None (xi) SEQUENCE DESCRIPTION: SEQ ID NO:20:

```
Thr Asp Leu Ile Gln Arg Pro Arg Arg Leu Arg Lys Ser Pro Ala Leu
  1               5                  10                  15

Pro Arg Met Phe Glu Glu Thr Thr Leu Ser Leu Asn Asp Leu Val Leu
             20                  25                  30

Pro Ile Phe Val Glu Glu Ile Asp Asp Tyr Lys Ala Val Glu Ala
             35                  40                  45

Met Pro Gly Val Met Arg Ile Pro Glu Lys His Leu Ala Arg Glu Ile
 50                  55                  60

Glu Arg Ile Ala Asn Ala Gly Ile Arg Ser Val Met Thr Phe Gly Ile
 65                  70                  75                  80

Ser His His Thr Asp Glu Thr Gly Glu Arg Ala Trp Arg Glu Asp Gly
                 85                  90                  95

Leu Val Ala Arg Met Ser Arg Ile Cys Lys Gln Thr Val Pro Glu Met
                100                 105                 110

Ile Val Met Ser Asp Thr Cys Phe Cys Glu Tyr Thr Ser His Gly His
                115                 120                 125

Cys Gly Val Leu Cys Glu His Gly Val Asp Asn Asp Ala Thr Leu Glu
    130                 135                 140

Asn Leu Gly Lys Gln Ala Val Val Ala Ala Ala Gly Ala Asp Phe
145                 150                 155                 160

Ile Ala Pro Ser Ala Ala Met Asp Gly Gln Val Gln Ala Ile Arg Gln
                165                 170                 175

Ala Leu Asp Ala Ala Gly Phe Lys Asp Thr Ala Ile Met Ser Tyr Ser
                180                 185                 190

Thr Lys Phe Ala Ser Ser Phe Tyr Gly Pro Phe Arg Glu Ala Ala Gly
            195                 200                 205

Ser Ala Leu Lys Gly Asp Arg Lys Ser Tyr Gln Met Asn Pro Met Asn
    210                 215                 220

Arg Ala Glu Gly Ile Ala Glu Tyr Leu Leu Asp Glu Ala Gln Gly Ala
225                 230                 235                 240

Asp Cys Leu Met Val Lys Pro Ala Gly Ala Tyr Leu Asp Ile Val Arg
                245                 250                 255

Glu Leu Arg Glu Arg Thr Glu Leu Pro Ile Gly Ala Tyr Gln Val Ser
            260                 265                 270

Gly Glu Tyr Ala Met Ile Lys Phe Ala Ala Leu Ala Gly Ala Ile Asp
        275                 280                 285

Glu Glu Lys Val Val Leu Glu Ser Leu Gly Ser Ile Lys Arg Ala Gly
    290                 295                 300

Ala Asp Leu Ile Phe Ser Tyr Phe Ala Leu Asp Leu Ala Glu Lys Lys
305                 310                 315                 320

Ile Leu Arg
```

(2) INFORMATION FOR SEQ ID NO:21:

(i) SEQUENCE CHARACTERISTICS:
        (A) LENGTH: 398 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:21:

His Thr Phe Val Asp Leu Lys Ser Pro Phe Thr Leu Ser Asn Tyr Leu

```
  1               5                    10                   15
Ser Phe Ser Ser Ser Lys Arg Arg Gln Pro Pro Ser Leu Phe Thr Val
            20                  25              30
Arg Ala Ser Asp Ser Asp Phe Glu Ala Val Val Ala Gly Lys Val
        35              40              45
Pro Glu Ala Pro Pro Val Pro Pro Thr Pro Ala Ser Pro Ala Gly Thr
    50              55              60
Pro Val Val Pro Ser Leu Pro Ile Gln Arg Arg Pro Arg Arg Asn Arg
65              70              75                       80
Arg Ser Pro Ala Leu Arg Ser Ala Phe Gln Glu Thr Thr Leu Ser Pro
            85              90              95
Ala Asn Phe Val Tyr Pro Leu Phe Ile His Glu Gly Glu Glu Asp Thr
            100             105             110
Pro Ile Gly Ala Met Pro Gly Cys Tyr Arg Leu Gly Trp Arg His Gly
            115             120             125
Leu Leu Glu Glu Val Ala Lys Ala Arg Asp Val Gly Val Asn Ser Val
        130             135             140
Val Leu Phe Pro Lys Ile Pro Asp Ala Leu Lys Thr Pro Thr Gly Asp
145             150             155                      160
Glu Ala Tyr Asn Glu Asp Gly Leu Val Pro Arg Ser Ile Arg Leu Leu
            165             170             175
Lys Asp Lys Tyr Pro Asp Leu Ile Ile Tyr Thr Asp Val Ala Leu Asp
            180             185             190
Pro Tyr Ser Ser Asp Gly His Asp Gly Ile Val Arg Glu Asp Gly Val
        195             200             205
Ile Met Asn Asp Glu Thr Val His Gln Leu Cys Lys Gln Ala Val Ala
    210             215             220
Gln Ala Arg Ala Gly Ala Asp Val Val Ser Pro Ser Asp Met Met Asp
225             230             235                      240
Gly Arg Val Gly Ala Met Arg Val Ala Leu Asp Ala Glu Gly Phe Gln
            245             250             255
His Val Ser Ile Met Ser Tyr Thr Ala Lys Tyr Ala Ser Ser Phe Tyr
        260             265             270
Gly Pro Phe Arg Glu Ala Leu Asp Ser Asn Pro Arg Phe Gly Asp Lys
    275             280             285
Lys Thr Tyr Gln Met Asn Pro Ala Asn Tyr Arg Glu Ala Leu Thr Glu
    290             295             300
Met Arg Glu Asp Glu Ser Glu Gly Ala Asp Ile Leu Leu Val Lys Pro
305             310             315                      320
Gly Leu Pro Tyr Leu Asp Ile Ile Arg Leu Leu Arg Asp Asn Ser Pro
            325             330             335
Leu Pro Ile Ala Ala Tyr Gln Val Ser Gly Glu Tyr Ser Met Ile Lys
            340             345             350
Ala Gly Gly Ala Leu Lys Met Ile Asp Glu Glu Lys Val Met Met Glu
            355             360             365
Ser Leu Leu Cys Leu Arg Arg Ala Gly Ala Asp Ile Ile Leu Thr Tyr
            370             375             380
Phe Ala Leu Gln Ala Ala Arg Thr Leu Cys Gly Glu Lys Arg
385             390             395
```

(2) INFORMATION FOR SEQ ID NO:22:

(i) SEQUENCE CHARACTERISTICS:
        (A) LENGTH: 323 amino acids

```
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:22:

Met Ser Gln Ser Phe Asn Arg His Arg Leu Arg Thr Ser Lys Ala
 1               5                  10                  15

Met Arg Glu Met Val Lys Glu Thr Arg Leu His Pro Ser Asp Phe Ile
            20                  25                  30

Tyr Pro Ile Phe Val Val Glu Gly Leu Glu Gly Lys Lys Ala Val Pro
            35                  40                  45

Ser Met Pro Asp Val His His Val Ser Leu Asp Leu Leu Lys Asp Glu
 50                  55                  60

Val Ala Glu Leu Val Lys Leu Gly Ile Gln Ser Val Ile Val Phe Gly
 65                  70                  75                  80

Ile Pro Glu Glu Lys Asp Asp Cys Gly Thr Gln Ala Tyr His Asp His
                85                  90                  95

Gly Ile Val Gln Lys Ala Ile Thr Glu Ile Lys Glu His Phe Pro Glu
                100                 105                 110

Met Val Val Ala Asp Thr Cys Leu Cys Glu Tyr Thr Asp His Gly
            115                 120                 125

His Cys Gly Leu Val Lys Asp Gly Val Ile Leu Asn Asp Glu Ser Leu
 130                 135                 140

Glu Leu Leu Ala Gln Thr Ala Val Ser Gln Ala Lys Ala Gly Ala Asp
145                 150                 155                 160

Ile Ile Ala Pro Ser Asn Met Met Asp Gly Phe Val Thr Val Ile Arg
                165                 170                 175

Glu Ala Leu Asp Lys Glu Gly Phe Val Asn Ile Pro Ile Met Ser Tyr
                180                 185                 190

Ala Val Lys Tyr Ser Ser Glu Phe Tyr Gly Pro Phe Arg Asp Ala Ala
                195                 200                 205

Asn Ser Thr Pro Gln Phe Gly Asp Arg Lys Thr Tyr Gln Met Asp Pro
 210                 215                 220

Ala Asn Arg Met Glu Ala Leu Arg Glu Ala Gln Ser Asp Val Glu Glu
225                 230                 235                 240

Gly Ala Asp Phe Leu Ile Val Lys Pro Ser Leu Ser Tyr Met Asp Ile
                245                 250                 255

Met Arg Asp Val Lys Asn Glu Phe Thr Leu Pro Leu Val Ala Tyr Val
            260                 265                 270

Ser Gly Glu Tyr Ser Met Val Lys Ala Ala Ala Gln Asn Gly Trp Ile
            275                 280                 285

Lys Glu Lys Glu Ile Val Leu Glu Ile Leu Thr Ser Met Lys Arg Ala
            290                 295                 300

Gly Ala Asp Leu Ile Ile Thr Tyr His Ala Lys Asp Ala Ala Lys Trp
305                 310                 315                 320

Leu Ala Glu (2) INFORMATION FOR SEQ ID NO:23:

(i) SEQUENCE CHARACTERISTICS:
        (A) LENGTH: 424 amino acids
        (B) TYPE: amino acid
        (C) STRANDEDNESS: single
        (D) TOPOLOGY: linear
```

(ii) MOLECULE TYPE: None (xi) SEQUENCE DESCRIPTION: SEQ ID NO:23:

```
Met Met Ala Ser Thr Phe Asn Ile Pro Cys Asn Ala Gly Thr Ile Lys
 1               5                  10                  15

Asn Phe Asn Asn Ser Gln Arg Asn Leu Gly Phe Ser Ser Asn Leu Gly
            20                  25                  30

Ile Asn Phe Ala Lys Thr Arg Phe Ser Asn Cys Gly Asp Ser Gly Arg
        35                  40                  45

Ile Pro Ser Gln Leu Val Val Arg Ala Ser Glu Arg Arg Asp Asn Leu
    50                  55                  60

Thr Gln Gln Lys Thr Gly Leu Ser Ile Glu Glu Cys Glu Ala Ala Val
65                  70                  75                  80

Val Ala Gly Asn Ala Pro Ser Ala Pro Pro Val Pro Thr Pro Lys
                85                  90                  95

Ala Pro Ser Gly Thr Pro Ser Val Ser Pro Leu Ser Leu Gly Arg Arg
            100                 105                 110

Pro Arg Arg Asn Arg Thr Ser Pro Val Phe Arg Ala Ala Phe Gln Glu
        115                 120                 125

Thr Thr Leu Ser Pro Ala Asn Val Val Tyr Pro Leu Phe Ile His Glu
    130                 135                 140

Gly Glu Glu Asp Thr Pro Ile Gly Ala Met Pro Gly Cys Tyr Arg Leu
145                 150                 155                 160

Gly Trp Arg His Gly Leu Val Glu Glu Val Ala Lys Ala Arg Asp Val
                165                 170                 175

Val Val Asn Ser Ile Val Val Phe Pro Lys Pro Asp Ala Leu Lys Ser
            180                 185                 190

Pro Thr Gly Asp Glu Ala Tyr Asn Glu Asn Gly Leu Val Pro Arg Thr
        195                 200                 205

Ile Arg Met Leu Lys Asp Lys Phe Pro Asp Leu Ile Ile Tyr Thr Asp
    210                 215                 220

Val Ala Leu Asp Pro Tyr Tyr Tyr Asp Gly His Asp Gly Ile Val Thr
225                 230                 235                 240

Gln His Gly Val Ile Met Asn Asp Glu Thr Val His Gln Leu Cys Lys
                245                 250                 255

Gln Ala Val Ala Gln Ala Arg Ala Gly Ala Asp Val Val Ser Pro Ser
            260                 265                 270

Asp Met Met Asp Gly Arg Val Gly Ala Ile Arg Ala Ala Leu Asp Ala
        275                 280                 285

Glu Gly Tyr Ser Asn Val Ser Ile Met Ser Tyr Thr Ala Lys Tyr Ala
    290                 295                 300

Ser Ser Phe Tyr Pro Arg Phe Gly Asp Lys Lys Thr Tyr Gln Met Asn
305                 310                 315                 320

Pro Ala Asn Tyr Arg Glu Ala Leu Ile Glu Thr Gln Glu Asp Glu Ser
                325                 330                 335

Glu Gly Ala Asp Ile Leu Leu Val Lys Pro Gly Leu Pro Tyr Leu Asp
            340                 345                 350

Ile Ile Arg Leu Leu Arg Asp Asn Ser Asp Leu Pro Ile Ala Ala Tyr
        355                 360                 365

Gln Val Ser Gly Glu Tyr Ser Met Ile Lys Ala Gly Gly Val Leu Lys
    370                 375                 380

Met Ile Asp Glu Gly Lys Val Met Leu Glu Ser Leu Leu Cys Leu Arg
385                 390                 395                 400
```

-continued

```
Arg Ala Gly Ala Asp Ile Ile Leu Thr Tyr Phe Ala Leu Gln Ala Ala
            405                 410                 415
Arg Cys Leu Cys Gly Glu Lys Arg
            420
```

ASPERGILLUS PORPHOBILINOGEN SYNTHASES AND NUCLEIC ACIDS ENCODING SAME

CROSS-REFERENCE TO RELATED APPLICATIONS

This application is a divisional of application Ser. No. 08/871,268 filed on Jun. 9, 1997, now U.S. Pat. No. 5,866, 391 issued on Feb. 2, 1999, and claims priority under 35 U.S.C. 119 of U.S. application Ser. No. 60/019,529 filed Jun. 10, 1996, the contents of which are fully incorporated herein by reference.

BACKGROUND OF THE INVENTION

1. Field of the Invention

The present invention relates to Aspergillus porphobilinogen synthases and isolated nucleic acid fragments comprising nucleic acid sequences encoding the porphobilinogen synthases. The invention also relates to nucleic acid constructs, vectors, and host cells comprising the nucleic acid sequences as well as methods for producing the porphobilinogen synthases.

2. Description of the Related Art

Heme, a chelate complex of protoporphyrin IX and iron, serves as a prosthetic group of hemoproteins. Protoporphyrin IX consists of a porphyrin ring, substituted with four methyl groups, two vinyl groups, and two propionic acid groups, which acquires an iron atom to form heme. The biosynthesis of heme from glycine and succinyl-CoA involves eight enzymatic steps. The second enzyme in the pathway is porphobilinogen synthase (also called aminolevulinic acid dehydratase) which catalyzes the condensation of two molecules of 5-aminolevulinic acid to form porphobilinogen. Porphobilinogen synthase is a rate-limiting enzyme in the heme biosynthesis pathways of Neurospora crassa and Saccharomyces cerevisiae.

The conversion of an apoprotein into a hemoprotein depends on the availability of heme provided by the heme biosynthetic pathway. The apoprotein form of the hemoprotein combines with heme to produce the active hemoprotein. The active hemoprotein acquires a conformation which makes the hemoprotein more stable than the apoprotein to proteolytic attack. If the amount of heme produced by a microorganism is less relative to the amount of the apoprotein produced, the apoprotein will accumulate and undergo proteolytic degradation lowering the yield of the active hemoprotein.

In order to overcome this problem, Jensen showed that the addition of heme or a heme-containing material to a fermentation medium led to a significant increase in the yield of a peroxidase produced by Aspergillus oryzae (WO 93/19195). While heme supplementation of a fermentation medium results in a significant improvement in the yield of a hemoprotein, it is non-kosher, costly, and difficult to implement on a large scale.

The cloning and expression of a porphobilinogen synthase gene from Saccharomyces cerevisiae (Labbe-Bois and Labbe, 1990, In, Dailey, H. A., ed., Biosynthesis of Heme and Chlorophylls, McGraw-Hill, Inc., New York, page 258) has been disclosed.

It is an object of the present invention to provide new porphobilinogen synthases and genes encoding same.

SUMMARY OF THE INVENTION

The present invention relates to substantially pure porphobilinogen synthases obtained from Aspergillus and to isolated nucleic acid fragments comprising a nucleic acid sequence which encodes an Aspergillus porphobilinogen synthase. The present invention further provides nucleic acid constructs, vectors, and recombinant host cells comprising a nucleic acid fragment of the present invention as well as methods for producing the porphobilinogen synthases.

BRIEF DESCRIPTION OF THE FIGURES

FIG. 2 shows the nucleotide and deduced amino acid sequence of the Aspergillus oryzae porphobilinogen synthase gene (SEQ ID NOS:1 and 2, respectively). CAAT boxes are underlined and TATA boxes are boxed. The putative intron is identified with a dotted underline and the putative zinc finger domain is identified with a dashed underline. The library probe is identified with a dark solid underline and the active lysine is circled.

FIG. 3 shows the alignment of the deduced amino acid sequences for porphobilinogen synthases from B. subtilis, E. coli, human, pea, rat, spinach, yeast and Aspergillus oryzae (SEQ ID NOS:22, 20, 18, 21, 19, 23, 17 and 2, respectively).

DETAILED DESCRIPTION OF THE INVENTION

Figure 1:
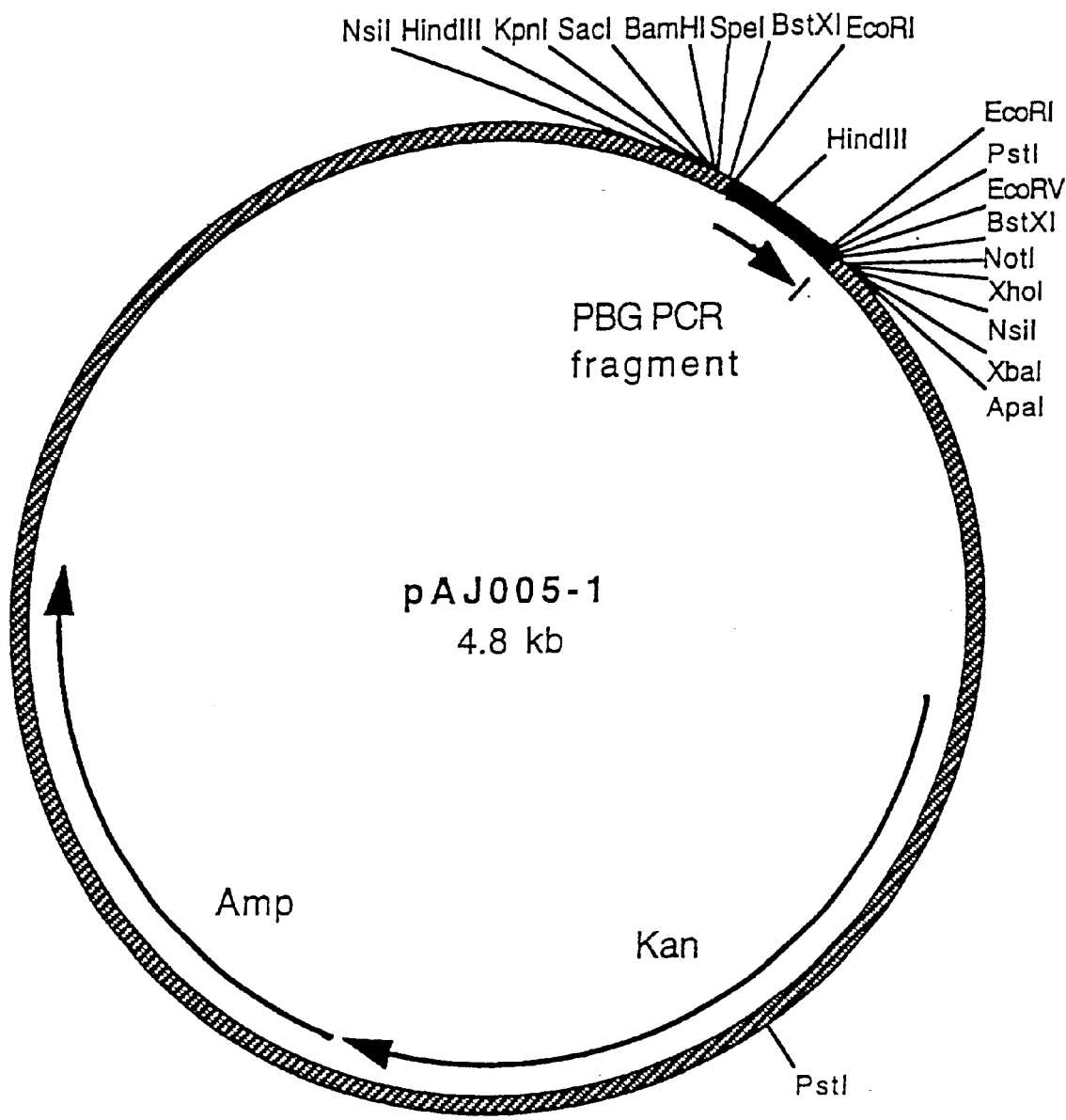
FIG. 1 shows a restriction map of plasmid pAJ005-1.

The present invention, as mentioned above, relates to porphobilinogen synthases obtained from an Aspergillus strain, e.g., porphobilinogen synthases obtained from strains of including, but not limited to, Aspergillus foetidus, Aspergillus japonicus, Aspergillus nidulans, Aspergillus niger, and Aspergillus oryzae. Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), International Mycological Institute (IMI), Agricultural Research Service Patent Culture Collection, Northern Regional Research Center (NRRL), and Institute for Fermentation in Osaka, Japan (IFO).

In a preferred embodiment, the present invention relates to porphobilinogen synthases obtained from Aspergillus. In a more preferred embodiment, the present invention relates to porphobilinogen synthases obtained from Aspergillus oryzae. In a most preferred embodiment, the present invention relates to porphobilinogen synthases obtained from Aspergillus oryzae IFO 4177 or a mutant strain thereof, e.g., the porphobilinogen synthase having the amino acid sequence set forth in SEQ ID NO:2.

The present invention also relates to porphobilinogen synthases which are encoded by nucleic acid sequences which are capable of hybridizing under high stringency conditions (i.e., prehybridization and hybridization at 45° C. in 5×SSPE, 0.3% SDS, 200 µg/ml sheared and denatured salmon sperm DNA, and 50% formamide) with a probe which hybridizes with the nucleic acid sequence set forth in SEQ ID NO:1 under the same conditions. The gene, or an oligonucleotide based thereon, can be used as a probe in Southern hybridization to isolate homologous genes of any Aspergillus species. In particular, such probes can be used for hybridization with the genomic or cDNA of the species of interest, following standard Southern blotting procedures, in order to identify and isolate the corresponding porphobilinogen synthase gene therein. Degenerate PCR primers (oligonucleotides) can be used with genomic DNA or cDNA segments to amplify porphobilinogen synthase-specific gene segments.

Identification and isolation of porphobilinogen synthase genes from a source other than those specifically exemplified herein can be achieved by utilization of the methodology described in the present examples, with publicly available Aspergillus strains.

For purposes of the present invention, the term "obtained from" means that the porphobilinogen synthase is produced by a specific source, e.g., an Aspergillus strain, or by a cell in which a gene from the source encoding the porphobilinogen synthase has been inserted.

The invention also encompasses porphobilinogen synthase variants which have at least about 50%, preferably about 55%, more preferably about 60%, even more preferably about 65%, yet even preferably about 70%, further preferably about 75%, even further preferably about 80%, and most preferably about 85%, even most preferably about 90%, and yet even most preferably about 95% homology with the amino acid sequence set forth in SEQ ID NO:2, and which qualitatively retains the activity of the porphobilinogen synthases described herein. The present invention is also directed to porphobilinogen synthase variants which have an amino acid sequence which differs by three amino acids, preferably two amino acids, and more preferably by one amino acid from the amino acid sequence set forth in SEQ ID NO:2. Each difference may be an insertion or deletion of an amino acid or the substitution of an amino acid residue by a different amino acid. Useful variants within the categories defined above include, for example, ones in which conservative amino acid substitutions have been made, which substitutions do not significantly affect the activity of the protein. By conservative substitution is meant that amino acids of the same class may be substituted by any other amino acid of that class. For example, the nonpolar aliphatic residues Ala, Val, Leu, and Ile may be interchanged, as may be the basic residues Lys and Arg, or the acidic residues Asp and Glu. Similarly, Ser and Thr are conservative substitutions for each other, as are Asn and Gln.

The physical-chemical properties of the porphobilinogen synthases of the present invention may be determined using various techniques well known in the art including, but not limited to, SDS-PAGE, isoelectric focusing, and cross-reaction immunoidentity tests. The porphobilinogen synthases of the present invention may be assayed using methods known in the art.

The porphobilinogen synthases of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), or extractionl (see, for example, Protein Purification, eds. J. -C. Janson and Lars Ryden, VCH Publishers, New York, 1989). As defined herein, a "substantially pure" porphobilinogen synthase is a porphobilinogen synthase which is essentially free of other non-porphobilinogen synthase proteins, for example, at least about 20% pure, preferably about 40% pure, more preferably about 60% pure, even more preferably about 80% pure, most preferably about 90% pure, and even most preferably at least about 95% pure, as determined by SDS-PAGE.

The present invention also relates to nucleic acid fragments comprising a nucleic acid sequence which encodes a porphobilinogen synthase of the present invention and to nucleic acid constructs comprising a nucleic acid fragment of the present invention.

In a preferred embodiment, the nucleic acid sequence encodes a porphobilinogen synthase obtained from Aspergillus. In a more preferred embodiment, the nucleic acid sequence encodes a porphobilinogen synthase obtained from *Aspergillus oryzae*. In a most preferred embodiment, the nucleic acid sequence encodes a porphobilinogen synthase obtained from *Aspergillus oryzae* IFO 4177, e.g., the nucleic acid sequence set forth in SEQ ID NO:1. The present invention also encompasses nucleic acid sequences which encode a porphobilinogen synthase having the amino acid sequence set forth in SEQ ID NO:2, which differ from SEQ ID NO:1 by virtue of the degeneracy of the genetic code. The nucleic acid sequences of the present invention encompass both the genomic sequence depicted therein as well as the corresponding cDNA and RNA sequences, and the phrase "nucleic acid sequence" as used herein will be understood to encompass all such variations including synthetic DNA.

The present invention also relates to nucleic acid constructs comprising a nucleic acid fragment of the invention. "Nucleic acid construct" shall generally be understood to mean a nucleic acid molecule, either single- or double-stranded, which is isolated from a naturally occurring gene or which has been modified to contain segments of nucleic acid which are combined and juxtaposed in a manner which would not otherwise exist in nature. In a preferred embodiment, the nucleic acid constructs are operably linked to regulatory regions capable of directing the expression of the porphobilinogen synthase in a suitable expression host.

The present invention also provides recombinant vectors comprising a nucleic acid construct of the present invention. In a preferred embodiment, the nucleic acid sequence is operably linked to a promoter sequence. In another preferred embodiment, the vectors of the present invention further comprise a transcription termination signal and/or a selectable marker.

The recombinant vectors of the invention are useful for the expression of an Aspergillus porphobilinogen synthase gene in active form. A useful vector contains an element that permits stable integration of the vector into the host cell genome or autonomous replication of the vector in a host cell independent of the genome of the host cell, and preferably one or more phenotypic markers which permit easy selection of transformed host cells. The vector may also include control sequences such as a promoter, ribosome binding site, translation initiation signal, and, optionally, a selectable marker or various activator or repressor sequences. To permit the secretion of the expressed protein, nucleic acids encoding a signal sequence may be inserted prior to the coding sequence of the gene. For expression under the direction of control sequences, a porphobilinogen synthase gene to be used according to the present invention is operably linked to the control sequences in such a way that expression of the coding sequence is achieved under conditions compatible with the control sequences.

The vectors carrying a nucleic acid construct of the present invention may be any vector which can conveniently be subjected to recombinant DNA procedures. The choice of a vector will typically depend on the host cell into which the vector is to be introduced. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. Alternatively, the vector may be one which, when introduced into a host cell, is integrated into the host cell genome and replicated together with the chromosome(s) into which it has been integrated. The vector system may be a single vector or plasmid or two or more vectors or plasmids which together contain the total DNA to be integrated into the genome.

In the vectors, the DNA sequence should be operably linked to a suitable promoter sequence. The promoter may be any DNA sequence which shows transcriptional activity in the host cell of choice and may be obtained from genes encoding proteins either homologous or heterologous to the host cell. Examples of suitable promoters for directing the transcription of the nucleic acid construct of the invention, especially in a bacterial host, are the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), the promoters of the *Bacillus subtilis* xylA and xylB genes, the prokaryotic β-lactamase promoter (Villa-Kamaroff et al., 1978, *Proceedings of the National Academy of Sciences USA* 75:3727–3731) or the tac promoter (DeBoer et al., 1983, *Proceedings of the National Academy of Sciences USA* 80:21–25). Further promoters are described in "Useful proteins from recombinant bacteria" in *Scientific American*, 1980, 242:74–94; and in Sambrook et al., *Molecular Cloning, A Laboratory Manual*, 2d ed., Cold Spring Harbor, N.Y., 1989. In a yeast host, a useful promoter is the eno-1 promoter. For transcription in a fungal host, examples of useful promoters are those obtained from the genes encoding *Aspergillus oryzae* TAKA amylase, *Rhizomucor miehei* aspartic proteinase, *Aspergillus niger* neutral α-amylase, *Aspergillus niger* acid stable α-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase or *Aspergillus nidulans* acetamidase. Preferred promoters are the TAKA-amylase, NA2-tpi, and glaA promoters.

The vectors of the invention may also comprise a suitable transcription terminator and, in eukaryotes, polyadenylation sequences operably connected to the DNA sequence encoding a porphobilinogen synthase of the present invention. Termination and polyadenylation sequences may be obtained from the same sources as the promoter. The vectors may further comprise a DNA sequence enabling the vectors to replicate in the host cell in question. Examples of such sequences are the origins of replication of plasmids pUC19, pACYC177, pUB110, pE194, pAMB1, and pIJ702.

The vectors of the present invention preferably contain one or more selectable markers which permit easy selection of transformed cells. A selectable marker is a gene the product of which provides for biocide or viral resistance, resistance to heavy metals, prototrophy to auxotrophs and the like. The selectable marker may be selected from the group consisting of, but not limited to, amdS, pyrG, argB, niaD, sC, trpC, bar, and hygB. Preferred for use in an Aspergillus cell are the amdS and pyrG markers of *Aspergillus nidulans* or *Aspergillus oryzae* and the bar marker of *Streptomyces hygroscopicus*. Furthermore, selection may be accomplished by co-transformation, e.g., as described in WO 91/17243 where the selectable marker is contained in a separate vector.

The vectors of the invention preferably also contain a signal peptide coding region, which codes for an amino acid sequence linked to the amino terminus of the heme biosynthetic enzyme, permitting the localization of the porphobilinogen synthase to a particular cellular compartment. The signal peptide coding region may be native to the first nucleic acid sequence encoding the porphobilinogen synthase or may be obtained from foreign sources. The 5' end of the coding sequence of the first nucleic acid sequence may inherently contain a signal peptide coding region naturally linked in translation reading frame with the segment of the coding region which encodes the localized porphobilinogen synthase. Alternatively, the 5' end of the coding sequence may contain nucleic acids encoding a signal peptide coding region which is foreign to that portion of the coding sequence which encodes the localized porphobilinogen synthase. The signal peptide coding region may be obtained from a *Neurospora crassa* ATPase gene (Viebrock et al., 1982, *EMBO Journal* 1:565–571) or from a *Saccharomyces cerevisiae* cytochrome c peroxidase gene (Kaput et al., 1982, *Journal of Biological Chemistry* 257:15054–15058). However, any signal peptide coding region capable of permitting localization of the 5-aminolevulinic acid synthase in a filamentous fungal host of choice may be used in the present invention.

To avoid the necessity of disrupting the cell to obtain the expressed porphobilinogen synthase, and to minimize the amount of possible degradation of the expressed porphobilinogen synthase within the cell, it is preferred that expression of the porphobilinogen synthase gene gives rise to a product secreted outside the cell. To this end, the porphobilinogen synthases of the present invention may thus, comprise a preregion permitting secretion of the expressed protein into the culture medium. If desirable, this preregion may be native to the porphobilinogen synthase of the invention or substituted with a different preregion or signal sequence, conveniently accomplished by substitution of the DNA sequences encoding the respective preregions. For example, the preregion may be obtained from a glucoamylase or an amylase gene from an Aspergillus species, an amylase gene from a Bacillus species, a lipase or proteinase gene from *Rhizomucor miehei*, the gene for the α-factor from *Saccharomyces cerevisiae* or the calf preprochymosin gene. Particularly preferred is the preregion for *Aspergillus oryzae* TAKA amylase, *Aspergillus niger* neutral amylase, the maltogenic amylase from Bacillus NCIB 11837, *Bacillus stearotherrnophilus* α-amylase, or *Bacillus licheniformis* subtilisin. An effective signal sequence for fungal hosts is the *Aspergillus oryzae* TAKA amylase signal, the *Rhizomucor miehei* aspartic proteinase signal, or the *Rhizomucor miehei* lipase signal.

The procedures used to ligate the nucleic acid construct of the invention, the promoter, terminator and other elements, and to insert them into suitable vectors containing the information necessary for replication, are well known to persons of ordinary skill in the art (cf., for instance, Sambrook et al., supra).

The present invention also relates to host cells comprising a nucleic acid construct or an expression vector of the invention which are advantageously used in the recombinant production of the porphobilinogen synthases of the invention. The cell may be transformed with the nucleic acid construct of the invention, conveniently by integrating the construct into the host chromosome. This integration is generally considered to be an advantage as the sequence is more likely to be stably maintained in the cell. Integration of the construct into the host chromosome may be performed according to conventional methods, e.g., by homologous or non-homologous recombination. Alternatively, the cell may be transformed with an expression vector as described below in connection with the different types of host cells.

The choice of host cells and vectors will to a large extent depend upon the porphobilinogen synthase and its source. The host cell may be selected from prokaryotic cells, such as bacterial cells. Examples of suitable bacteria are gram-positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis*, or *Streptomyces lividans* or *Streptomyces murinus*, or gram-negative bacteria such as *E. coli*. The transformation of the bacteria may, for instance, be effected by protoplast transformation or by using competent cells in a manner known per se.

The host cell is preferably a eukaryote, such as a mammalian cell, an insect cell, a plant cell or preferably a fungal cell, including yeast and filamentous fungi. For example, useful mammalian cells include CHO or COS cells. A yeast host cell may be selected from a species of Saccharomyces or Schizosaccharomyces, e.g., *Saccharomyces cerevisiae*. Useful filamentous fungi may be selected from a species of Aspergillus, e.g., *Aspergillus oryzae* or *Aspergillus niger*. Alternatively, a strain of a Fusarium species, e.g., *Fusarium oxysporum* or *Fusarium graminearum*, can be used as a host cell. Fungal cells may be transformed by a process involving protoplast formation, transformation of the protoplasts, and regeneration of the cell wall in a manner known per se. A suitable procedure for transformation of Aspergillus host cells is described in EP 238 023. A suitable method of transforming Fusarium species is described by Malardier et al., 1989, *Gene* 78:147–156 or in copending U.S. Ser. No. 08/269,449.

In a particularly preferred embodiment, the expression of the porphobilinogen synthase gene is achieved in a fungal host cell, such as Aspergillus. The porphobilinogen synthase gene is ligated into a plasmid preferably containing the *Aspergillus oryzae* TAKA amylase promoter or the *Aspergillus niger* neutral amylase NA2 promoter and amdS or pyrG as the selectable marker. Alternatively, the selectable marker may be on a separate plasmid and used in co-transformation. The plasmid (or plasmids) is used to transform an Aspergillus species host cell, such as *Aspergillus oryzae* or *Aspergillus niger* in accordance with methods described in Yelton et al., 1984, *Proceedings of the National Academy of Sciences USA* 81:1470–1474.

The present invention also relates to methods for producing a porphobilinogen synthase of the present invention comprising (a) cultivating an Aspergillus strain in a nutrient medium to produce the porphobilinogen synthase, and (b) recovering the porphobilinogen synthase.

The present invention also relates to methods for recombinantly producing a porphobilinogen synthase of the present invention comprising (a) cultivating a host cell comprising a nucleic acid construct which comprises a nucleic acid sequence encoding the porphobilinogen synthase under conditions conducive to the production of the enzyme, and (b) recovering the porphobilinogen synthase. If the expression system secretes the porphobilinogen synthase into the fermentation medium, the enzyme can be recovered directly from the medium. If the recombinant porphobilinogen synthase is not secreted, it is recovered from cell lysates.

Any method of cultivation of a cell known in the art may be used which results in the expression or isolation of a porphobilinogen synthase of the present invention. For example, cultivation may be understood as comprising shake flask cultivation, small- or large-scale fermentation (including continuous, batch, fed-batch, or solid state fermentations) in laboratory or industrial fermentors performed in a suitable medium and under conditions allowing the porphobilinogen synthase to be expressed or isolated. The cultivation takes place in a suitable nutrient medium comprising carbon and nitrogen sources and inorganic salts using procedures known in the art (see, e.g., Bennett, J. W. and LaSure, L. (eds.), *More Gene Manipulations in Fungi*, Academic Press, Calif., 1991). Suitable media are available from commercial suppliers or may be prepared according to published compositions (e.g., in catalogues of the American Type Culture Collection).

The porphobilinogen synthases produced by the methods described above may be recovered from the fermentation medium by conventional procedures including, but not limited to, centrifugation, filtration, spray-drying, evaporation, or precipitation. The recovered protein may then be further purified by a variety of chromatographic procedures, e.g., ion exchange chromatography, gel filtration chromatography, affinity chromatography, or the like.

The present invention is also directed to methods of using the porphobilinogen synthases.

The porphobilinogen synthases of the present invention may be used to increase the yield of a hemoprotein produced by a host cell, where porphobilinogen synthase is a rate-limiting step in the production of heme in the host cell, by overexpressing the nucleic acid sequence encoding the porphobilinogen synthase in the host cell. The method comprises:

(a) introducing into the host cell, which is capable of producing the hemoprotein, one or more copies of the nucleic acid sequence encoding the porphobilinogen synthase, wherein the nucleic acid sequence is operably linked to regulatory regions capable of directing the expression of the porphobilinogen synthase;

(b) cultivating the cell in a nutrient medium suitable for production of the hemoprotein and the porphobilinogen synthase; and (c) recovering the hemoprotein from the nutrient medium of the cell.

The present invention is further described by the following examples which should not be construed as limiting the scope of the invention.

EXAMPLES

Example 1

*Aspergillus oryzae* strain A1560 genomic DNA extraction

*Aspergillus oryzae* strain A1560 (IFO 4177) was grown in 25 ml of 0.5% yeast extract-2% glucose (YEG) medium for 24 hours at 32° C. and 250 rpm. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia which were subsequently frozen in liquid nitrogen. The frozen mycelia were ground to a fine powder in an electric coffee grinder, and the powder was added to 20 ml of TE buffer and 5 ml of 20% w/v sodium dodecylsulfate (SDS) in a disposable plastic centrifuge tube. The mixture was gently inverted several times to insure mixing, and extracted twice with an equal volume of phenol: chloroform: isoamyl alcohol (25:24:1 v/v/v). Sodium acetate (3 M solution) was added to a fmal concentration of 0.3 M followed by addition of 2.5 volumes of ice cold ethanol to precipitate the nucleic acids. The nucleic acids were then pelleted by centrifuging the tube at 15,000×g for 30 minutes. The pellet was allowed to air dry for 30 minutes before resuspension in 0.5 ml of TE buffer. DNase-free ribonuclease A was added to a concentration of 100 µg/ml and the mixture was incubated at 37 ûC for 30 minutes. Proteinase K was then added at a concentration of 200 µg/ml and the mixture was incubated an additional hour at 37° C. Finally, the mixture was extracted twice with phenol:chloroform:isoamyl alcohol (25:24:1 v/v/v) before precipitating the DNA with sodium acetate and ethanol as described earlier. The DNA pellet was dried under vacuum, resuspended in TE buffer, and stored at 4° C. until further use.

Example 2

Generation of a genomic hemB probe by PCR

Degenerate PCR primers were designed based on the amino acid sequence flanking a 126 bp hemB fragment from *Aspergillus oryzae* (Jesper Vind, 1994, Ph.D. Dissertation, University of Copenhagen, Copenhagen, Denmark) and the homologous regions of yeast and human hemB clones (Myers et al., 1987, *Journal of Biological Chemistry* 262:16822–16829; Wetmur et al., 1986, *Proceedings of the National Academy of Sciences USA* 83:7703–7707). The oligonucleotide primers were synthesized using an Applied Biosystems Model 394 DNA/RNA Synthesizer. Sense, 5'-GT(AGCT)GC(AGCT)CC(AGCT)(AT)(CG)(AGCT)G A(CT)ATGATGGA-3' (SEQ ID NO:3) and antisense 5'-GC (AG)TC(AGCT)CG/T(AG)A A(AGCT)CC(AG)TA-3' (SEQ ID NO:4) primers were used to PCR amplify the hemB fragment using pJVi 60 (Vind, 1994, supra) as a template. The PCR reaction (50 µl) was composed of 10 mM Tris-HCl pH 8.3, 50 mM KCl, 1.5 mM MgCl$_2$, 0.01% w/v gelatin, 200 µM each of dATP, dCTP, dGTP, and dTTP, 500 ng of pJVi 60, and 50 pmol of each PCR primer described above. The reaction was incubated at 95° C. for 3 minutes and cooled to 80° C. Then 5 units of Taq polymerase were added. The reaction was incubated in a Perkin-Elmer 9600 Thermal Cycler programmed for 35 cycles each at 95° C. for 30 seconds, 45° C. for 1 minute, and 72° C. 1 minute. Following the last cycle the reaction was incubated at 72° C. for 5 minutes. A predicted 126 bp hemB PCR product was cloned into a pCRII vector to produce plasmid pAJ005-1 (FIG. 1).

Example 3

*Aspergillus oryzae* strain A1560 DNA libraries and identification of porphobilinogen synthase (hemB) clones

*Aspergillus oryzae* strain A1560 genomic DNA libraries were constructed using the bacteriophage cloning vector λZIPLOX™ (Life Technologies, Gaithersburg, Md.) according to the manufacturer's instructions using *E. coli* Y1090ZL cells as a host for plating and purification of recombinant bacteriophage and *E. coli* DH10Bzip for excision of individual pZL1-hemA clones. Total cellular DNA prepared as described in Example 1 was partially digested with Tsp509I and size-fractionated on a 1% agarose gel with 50 mM Tris-50 mM borate-1 mM disodium EDTA (TBE) buffer. DNA fragments migrating in the size range 4–7 kb were excised and eluted from the gel using PREP-A-GENE™ reagents (BioRad Laboratories, Hercules, Calif.). The eluted DNA fragments were ligated with EcoRI-cleaved and dephosphorylated λZIPLOX™ vector arms, and the ligation mixtures were packaged using commercial packaging extracts (Stratagene, La Jolla, Calif.). The packaged DNA libraries were plated and amplified in *E. coli* Y1090ZL cells. The unamplified genomic library contained 1×10$^6$ pfu/ml.

Bacteriophage DNA from approximately 8×10$^4$ plaques was transferred to duplicate circular Nytran Plus membranes (Schleicher & Schuell, Keene, N.H.) and probed with a $^{32}$P-labeled PCR product derived by amplifying the hemB fragment of pAJ005-1 (see Example 2) according to Mertz and Rashtchian (1994, *Analytical Biochemistry* 221:160–165). The amplification reaction (50 µl) contained the following components: 10 mM Tris-HCl pH 8.3, 50 mM KCl, 1.5 mM MgCl2, 0.01% (w/v) gelatin, 0.04 mM each of dATP, dCTP, dGTP, and dTTP, 5 µl of $^{32}$P-dCTP (3000 Ci/mole, 3.3 µM; Amersham, Arlington Heights, Ill.), and 50 pmole each of sense primer 5'-GTGGCTCCGAGTGATAT-3' (SEQ ID NO:5) and antisense primer 5'-GCATCGCGAAAAGGACCG-3' (SEQ ID NO:6). The reaction was heated to 95° C. for 3 minutes followed by the addition of 5 units of Taq polymerase. The reaction was then incubated in a Perkin-Elmer Thermal Cycler programmed for 30 cycles, each cycle at 95° C. for 1 minute, 55° C. for 1 minute, and 72° C. for 1 minute. The reaction solution was passed through a Sephadex G50 column (Pharmacia, Alameda, Calif.) to remove unincorporated nucleotides and then denatured and added to the hybridization buffer. Denatured probe (10$^6$ cpm/ml) was added to hybridization buffer and incubated overnight with prehybridized membranes. Prehybridization and hybridization was conducted at 42° C. in 5×SSC, 50 mM sodium phosphate pH 7, 5×Denhardt's solution, 0.1% (w/v) SDS, 5 mM EDTA pH 8, 10 µg/mL denatured salmon sperm DNA, and 50% formamide. Membranes were washed four times in 0.1×SSC, 0.1% SDS for 15 minutes at 42° C. Primary plaques that gave a positive signal were screened a second time and purified according to the manufacturer's instructions. Ten genomic clones that produced a positive signal were excised from the λZIPLOX™ vector as pZL derivatives according to the manufacturer's instructions (Bethesda Research Laboratories, Inc., Bethesda, Md.) and sequenced according to the method of Hattori and Sakaki (1986, *Analytical Biochemistry* 152:232–237). The pZL derivatives were designated pAJ007-1 through pAJ007-10. Clone *E. coli* DH5α pAJ007-6 contained a 3.7 kb genomic fragment based on restriction mapping and was further analyzed.

Example 4

Characterization of the porphobilinogen synthase (hemB) gene

*E. coli* DH5α pAJ007-6 described in Example 2 was subjected to DNA sequencing according to the procedure described in Example 2.

The nucleotide sequence of the cloned *Aspergillus oryzae* A1560 hemB gene revealed an open reading frame of 1308 nucleotides as shown in FIG. 2 (SEQ ID NO:1) encoding a 374 amino acid polypeptide with a predicted molecular weight of 40 kDa as shown in FIG. 2 (SEQ ID NO:2). The nucleotide sequence contains one 48 bp putative intron which is flanked by splice site consensus sequences and contains an internal consensus sequence as predicted by (Unkles, 1992, in *Applied Molecular Genetics of Filamentous Fungi*, Chapter 2, J. R. Kinghorn and G. Turner, editors, Blackie Academic and Professional Publications). The 3' splice site (TAG) is located 254 bp downstream of the Met, a 5' splice site (GTCCGC) is located 46 bp upstream of the 3' splice site, and the internal consensus sequence (TCTAAC) is located 30 bp downstream of the 5' splice site. The 5' untranslated region contains two CAAT motifs at positions −377 and −233 and may play an important role in transcriptional regulation (Gurr et al., 1987, supra). In addition, several putative TATA like boxes are found in the 3' untranslated region (−117, −208, −650). As expected, hemB does not appear to contain a leader sequence at the N-terminus since it is cytoplasmic in other organisms except plants (Bottemley and Muller-Eberhard, 1988, *Seminars in Hematology* 25:282–302).

Amino acid alignment of the *Aspergillus oryzae* hemB gene (SEQ ID NO:2) to other hemB genes is shown in FIG. 3. The deduced hemB amino acid sequences from yeast (SEQ ID NO:17; Myers et al., 1987, supra), human (SEQ ID NO:18; Wetmur et al., 1986, supra), rat (SEQ ID NO:19; Bishop et al., 1989, *Nucleic Acids Research* 14:10115) and *E. coli* (SEQ ID NO:20; Li et al., 2989, *Gene* 75:177–184) have 63%, 55%, 55% and 40% identity, respectively to the *Aspergillus oryzae* hemB amino acid sequence. The deduced hemB amino acid sequences from pea (SEQ ID NO:21; Bsese et al., 1991, *Journal of Biological Chemistry* 266:17060–17066), *Bacillus subtilis* (SEQ ID NO:22; Hansson et al., 1991, *Journal of Bacteriology* 173:2590–2599) and spinach (SEQ ID NO:23; Scharnburg and Schneider-Poetsch, 1991, *EMBL Data Library*) are less similar (40%, 39% and 33% identity, respectively). However, since both the pea and spinach hemB amino acid sequences contain an N-terminal chloroplast signal sequence, their similarity to the *Aspergillus oryzae* hemB would significantly increase if they are aligned as mature polypeptides. Based on these alignments, the active lysine site of the *Aspergillus oryzae* hemB is located at amino acid 299 (Jaffe, 1995, *Journal of Bioenergetics and Biomembranes* 27:169–179) and a conserved zinc-finger like domain as predicted by Berg (1986, *Nature* 319:264–265) is located at amino acids 166–180. The zinc-finger has been suggested to prevent oxidation of the sulfhydryl groups at the active site by binding $Zn^{+2}$ (Jaffe, 1995, supra). The corresponding domain in plant hemB's is proposed to bind $Mg^{2+}$ rather than $Zn^{2+}$ (Bsese et al., 1991, supra). Interestingly, the first residue of the hemB finger domain is a Thr (at position 166) which is conserved for this position in the plant metal-binding domain. However, the remaining positions in the hemB zinc finger domain are conserved.

Example 5

Construction of pAJ023

Figure 4:
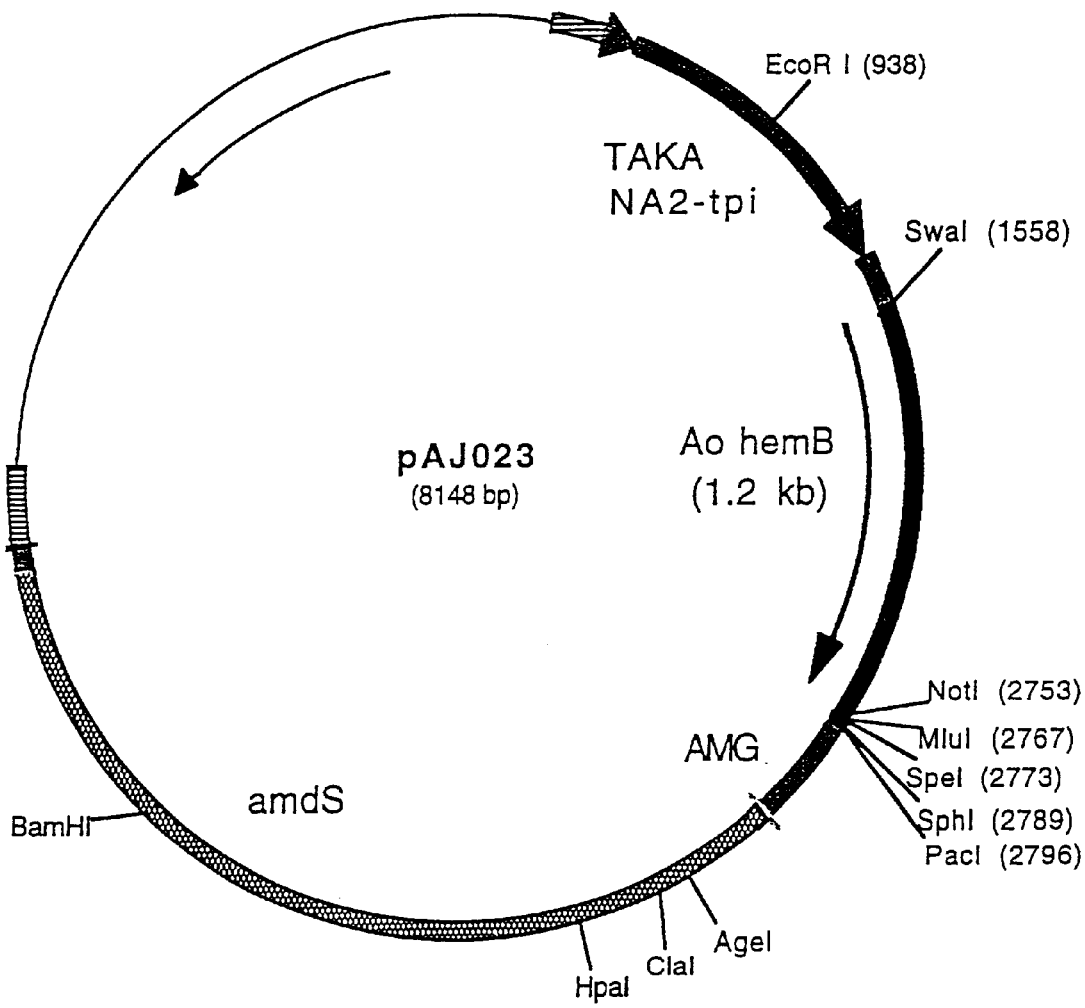
FIG. 4 shows a restriction map of pAJO23.

Plasmid pAJ023 (FIG. 4) was constructed by PCR amplifying the *Aspergillus oryzae* hemB coding region and subcloning it into the *Aspergillus oryzae* expression vector pBANE6. The amplification product was designed to contain 5' SwaI and 3' PacI restriction sites to facilitate cloning into pBANe6. The amplification reaction (50 μl) contained the following components: 10 mM Tris-HCl pH 8.3, 50 mM KCl, 1.5 mM $MgCl_2$, 0.01% (w/v) gelatin, 200 μM each of dATP, dCTP, dGTP, and dTTP, 200 ng of pAJ007-6 DNA, and 50 pmol of each PCR primer shown below:

PBG10 (Sense):
5'-GCATATTTAAATGATGTCCTTTTCTAATCT CGT-3' (SEQ ID NO:7)

PBG11A (Antisense):
5'-ATATTAATTAATCCATCTAGCTAAATCATT-3' (SEQ ID NO:8)

The underlined regions of PBG10 and PBG11A contained the cloning restriction sequences SwaI and PacI, respectively. The reaction was incubated at 95° C. for 3 minutes and cooled to 80° C. Five units of PWO (BM) polymerase were added. The reaction was incubated in a Perkin-Elmer 9600 Thermo-Cycler programmed for 30 cycles each at 95 ° C. for 30 seconds, 57° C. for 1 minute, and 72° C. for 1 minute. Following the last cycle, the reaction was incubated at 72° C. for 5 minutes. The final PCR product was gel purified, digested with SwaI and PacI, and ligated into the vector pBANE6 which was digested with SwaI and PacI to create pAJ023.

Example 6

Construction of *Aspergillus oryzae* strain JRoC50.3.18A

*Aspergillus oryzae* strain JRoC50.3.18A containing plasmid pJROC50 was constructed as follows. *Coprinus cinereus* IFO 8371 peroxidase cDNA fragments were prepared by PCR using specific oligonucleotide primers shown below (Saiki et al., 1988, *Science* 239:487–491) constructed on the basis of the amino acid sequence of the *Coprinus macrorhizus* peroxidase (Baunsgaard et al., 1993, *European Journal of Biochemistry* 213:605–611):

1. 5'-GCGCGAATTCGTNGGNATNGGNATNAA(CT) CA(CT)GG-3' (SEQ ID NO:9)

2. 3'-TACAGNTT(GA)AC(GA)GGNGGCCTAGGCG-5' (SEQ ID NO:10)

3. 5'-GCGAATTCACNCCNCA(GA)GTNTT(CT)GA (CT)AC-3' (SEQ ID NO:11)

4. 3'-GGNAA(GA)GGNCCNCT(CT)AA(GA) CCTAGGCG-5' (SEQ ID NO:12)

5. 5'-GCGCGAATTCTGGCA(GA)TCNAC-3' (SEQ ID NO:13)

6. 5'-GCGCGAATTCTGGCA(GA)AGNATG-3' (SEQ ID NO:14)

7. 3' -CGNTACCGNTT(CT)TACAGCCTAGG-5' (SEQ ID NO:15)

PCR was performed using the Gene Amp Kit and apparatus (Perkin Elmer Cetus, Norwalk, Conn.) in accordance with the manufacturer's instructions with the exception that the reaction was conducted at 28° C. for the first 3 cycles in order to obtain better hybridization to the first strand cDNA (prepared from MRNA obtained from *Coprinus cinereus* strain IFO 8371) and subsequently at 65° C. for 30 cycles of PCR.

The primers were combined as follows: 1 with 2; 3 with 4; 5 with 7; 6 with 7; 1 with 4; and 3 with 7. The PCR fragments were extended with an EcoRI site at the 5'-end and a BamHI site at the 3'-end. The reactions were analyzed on a 1% agarose-TBE gel where bands of the expected size were found in all the reactions. To verify that the bands corresponded to peroxidase-specific sequences, the gel was subjected to Southern blotting and hybridized to an oligonucleotide probe with the following sequence which is positioned between primers 3 and 4:

5'-GT(CT)TC(GA)AT(GA)TAGAA(CT)TG-3' (SEQ ID NO:16)

The probe was found to hybridize to bands of approximately 130 bp, 420 bp, 540 bp, and 240 bp, thus confirming that the DNA bands observed corresponded to peroxidase sequences.

DNA from the various PCR reactions was digested with EcoRI and BamHI and cloned into the plasmid pUC19 (New England BioLabs, Beverly, Mass.). Colonies containing the correct PCR fragments were identified by hybridization using the oligonucleotide probe (SEQ ID NO:16) described above. DNA from positive colonies was analyzed by restriction mapping and partial DNA sequence analysis as described by Sanger et al. (1977, *Proceedings of the National Academy of Sciences USA* 74:5463–5467). A 430 bp fragment from one of the clones, obtained by using primers 1 and 4, was used to screen a *Coprinus cinereus* cDNA library as described below.

Figure 5:
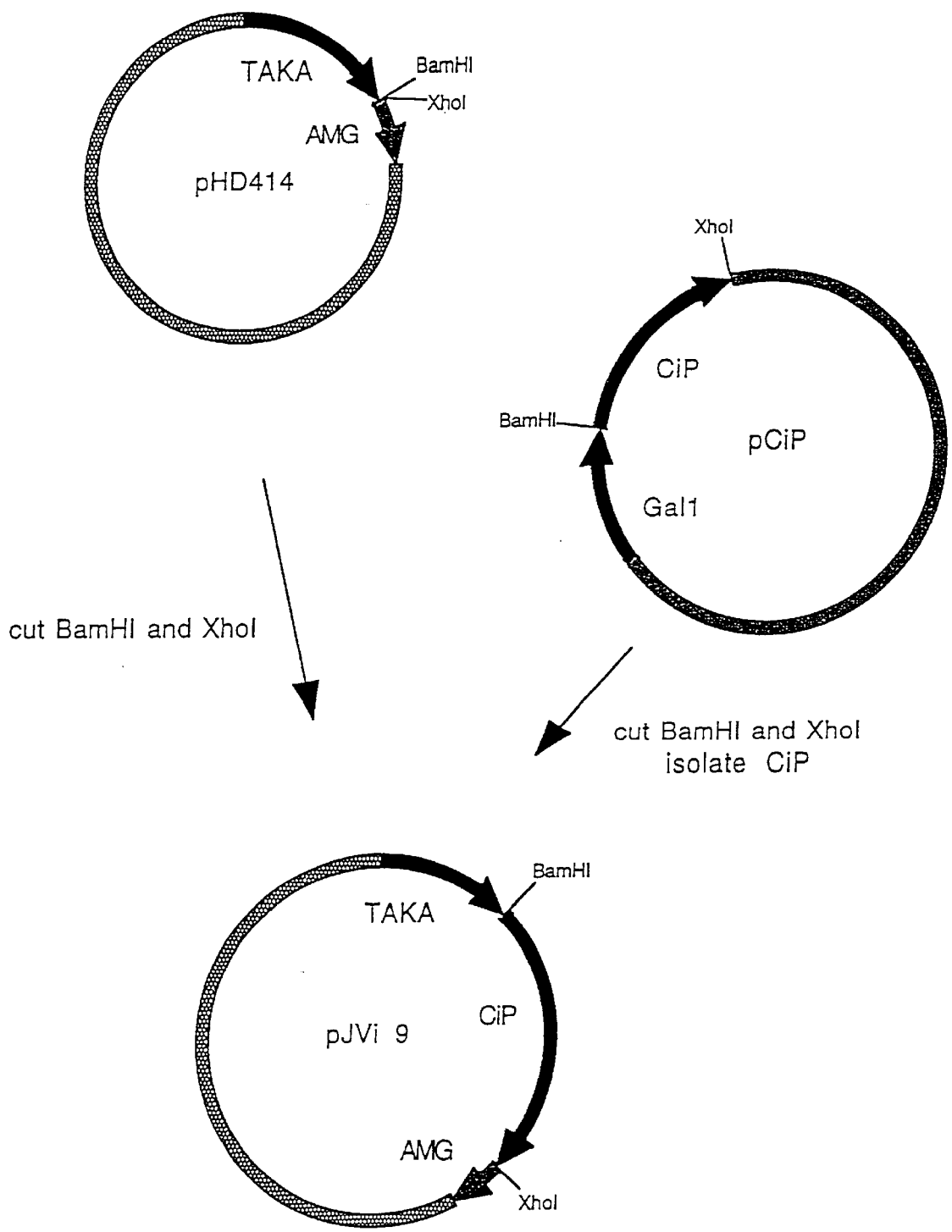
FIG. 5 shows the construction of plasmid pJVi9.

Total RNA was extracted from homogenized *Coprinus cinereus* strain IFO 8371 mycelia, collected at the time of maximum peroxidase activity according to the methods described by Boel et al. (1984, *EMBO Journal* 3:1097–1102) and Chirgwin et al. (1979, *Biochemistry* 18:5294–5299). Poly(A)-containing RNA was obtained by two cycles of affinity chromatography on oligo(dT)-cellulose as described by Aviv and Leder (1972, *Proceedings of the National Academy of Sciences USA* 69:1408–1412). cDNA was synthesized by means of a cDNA Synthesis Kit (Invitrogen, San Diego, Calif.) according to the manufacturer's instructions. Approximately 50,000 *E. coli* recombinants from the *Coprinus cinereus* cDNA library were transferred to Whatman 540 paper filters. The colonies were lysed and immobilized as described by Gerger et al. (1979, *Nucleic Acids Research* 7:2115–2135). The filters were hybridized with the $^{32}$P-labelled 430 bp peroxidase-specific probe in 0.2×SSC-0.1% SDS. Hybridization and washing of the filters was conducted at 65° C. followed by autoradiography for 24 hours with an intensifier screen. After autoradiography, the filters were washed at increasing temperatures followed by autoradiography for 24 hours with an intensifier screen. In this way, more than 50 positive clones were identified. Miniprep plasmid DNA was isolated from hybridizing colonies by standard procedures (Birnboim and Doly, 1979, *Nucleic Acids Research* 7:1513–1523), and the DNA sequences of the cDNA inserts were determined by the Sanger dideoxy procedure (Sanger et al., 1977, *Proceedings of the National Academy of Sciences USA* 74:5463–5467). One of the colonies was selected and the vector was designated pCiP. The peroxidase cDNA fragment was excised from the vector by cleavage with BamHI/XhoI and was purified by agarose gel electrophoresis, electroeluted and made ready for ligation reactions. The cDNA fragment was ligated to BamHI/XhoI digested pHD414 to generate pJVi9 wherein the cDNA was under transcriptional control of the TAKA promoter from *Aspergillus oryzae* and the AMG™ (Novo Nordisk A/S, Bagsvaerd, Denmark) terminator from *Aspergillus niger* as shown in FIG. 5.

Figure 6:
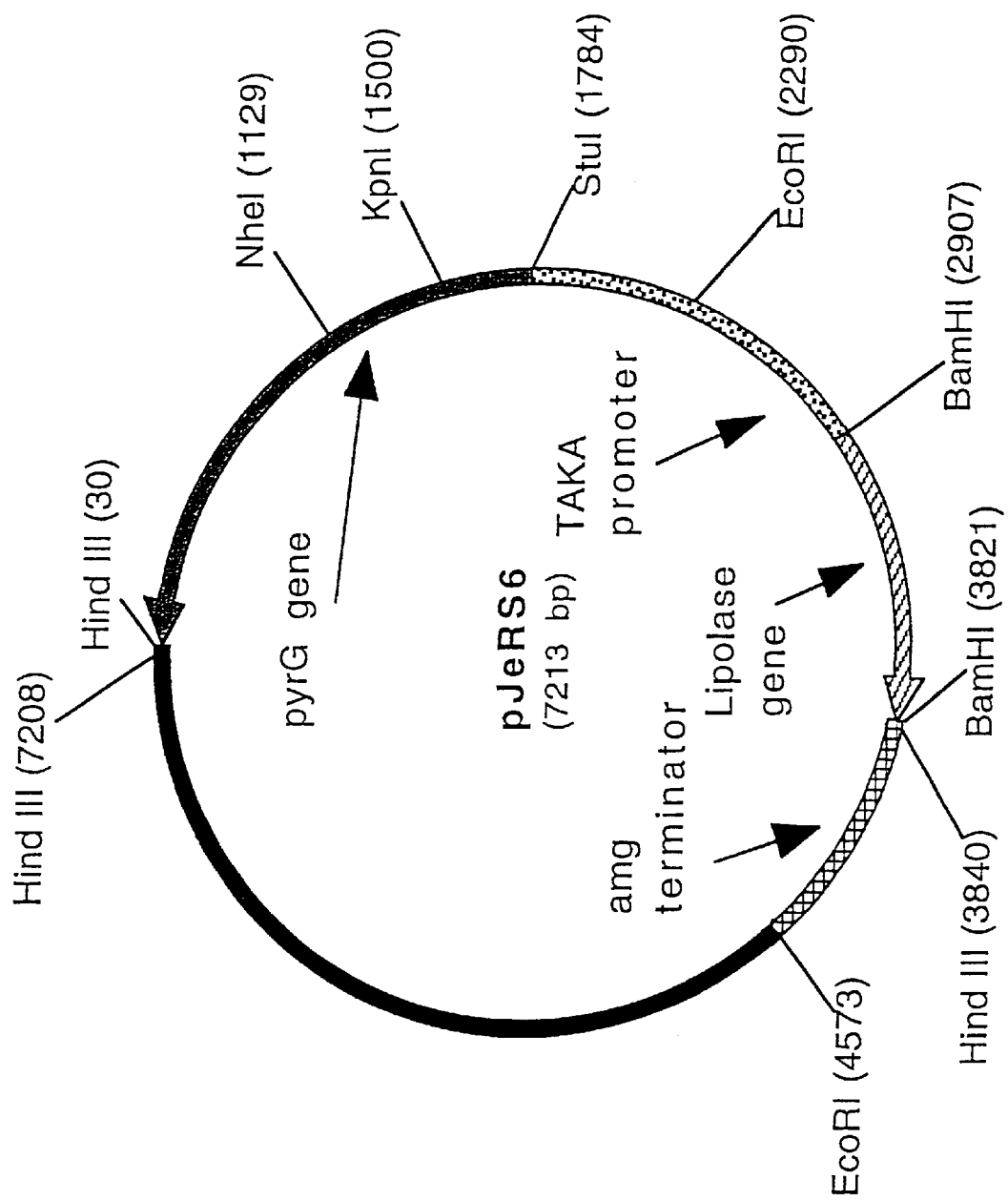
FIG. 6 shows a restriction map of plasmid pJeRS6.
Figure 7:
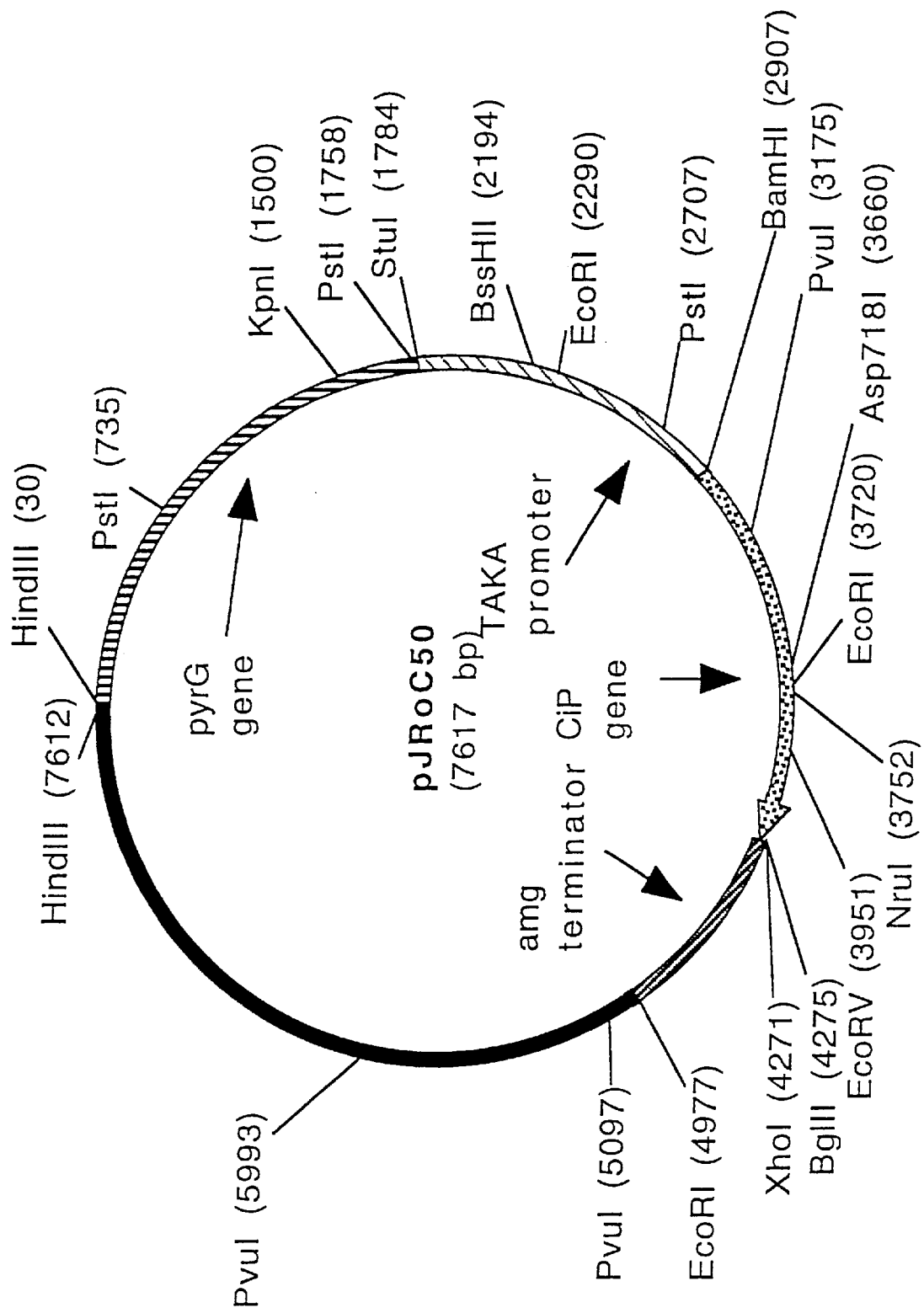
FIG. 7 shows a restriction map of plasmid pJRoC50.

The cDNA encoding the *Coprinus cinereus* peroxidase was excised from plasmid pJVi9 as a BamHI-XhoI fragment and cloned into plasmid pJeRS6 (FIG. 6) to produce plasmid pJRoC50 (FIG. 7) which contains pyrG as a selectable marker, the TAKA promoter, and the amdS terminator.

Transformants of *Aspergillus oryzae* strain HowB425 were made using 5 µg of purified plasmid pJRoC50 as described below with the following changes. The agar overlay was omitted and the protoplasts were plated directly on Minimal Medium plates. The transformation was conducted with protoplasts at a concentration of 2×10$^7$ protoplasts per ml. One hundred µl of protoplasts were placed on ice with 5 µg DNA for 30 minutes. One ml of SPTC (40% PEG 4000, 0.8 M sorbitol, 0.05 M Tris pH 8.0, 0.05 M CaCl$_2$) was added and the protoplasts were incubated at 34° C. for 20 minutes. The transformation was plated directly onto plates containing Minimal medium. The Minimal medium (pH 6.5) was composed of 6 g of NaNO$_3$, 0.52 g of KCl, 1.52 g of KH$_2$PO$_4$, 1 ml of trace metals, 1 g of glucose, 500 mg of MgSO$_4$-7H$_2$O, 342.3 g of sucrose, and 20 g of Noble agar per liter. The trace metals solution (1000×) was composed of 22 g of ZnSO$_4$-7H$_2$O, 11 g of H$_3$BO$_3$, 5 of MnCl$_2$-4H$_2$O, 5 g of FeSO$_4$-7H$_2$O, 1.6 g of CoCl$_2$-5H$_2$O, 1.6 g of (NH$_4$)$_6$Mo$_7$O$_{24}$, and 50 g of Na$_4$EDTA per liter. Plates were incubated 5–7 days at 34° C. Transformants were transferred to plates of the same medium and incubated 3–5 days at 37° C.

Sixty-six transformants were assayed for peroxidase activity using the following enzyme assay: 180 µl of substrate buffer {20 ml of 0.1 M potassium phosphate-0.01% Tween-80 pH 7.0, 250 µl of 2,2'-azinobis(3-ethylbenzothiazoline-6-sulfonate) (ABTS) solution (22 mg/ml), and 2 µl of 30% hydrogen peroxide} were added to 20 µl of culture supernatant which was diluted 1:900, quickly followed by measurement of the absorbance at 405 nm at 25° C. using a Molecular Devices Thermomax Microplate Reader (Molecular Devices, Sunnyvale, Calif.). Measurements were recorded every 10 seconds over a 2 minute period with mixing and V$_{max}$ values were calculated using the SOFTmax program (Molecular Devices, Sunnyvale, Calif.). The peroxidase units (POXU) per ml were estimated using a standard curve constructed with a known amount of *Cinereus coprinus* peroxidase as a standard. A POXU was defined as the amount of enzyme that catalyzes the conversion of 1.0 µmole per minute of 0.88 mM H$_2$O$_2$, 1.67 mM ABTS, 0.1 M phosphate pH 7.0 at 30° C. The four transformants expressing the highest levels were spore purified by streaking spores and picking isolated colonies using the same plates under the same conditions described above.

Final evaluations were performed in shake flasks where approximately 5×10$^6$ spores of each transformant were inoculated into 25 ml of MY25 medium containing 1% yeast extract, 2.5% maltose, 0.2% urea, and 1X MY salts pH 6.5. 1X MY salts was composed of 2 g of MgSO$_4$-7H$_2$0, 2 g of K$_2$PO$_4$, 10 g of KH$_2$PO$_4$, 2 g of citric of trace metals solution and 1 ml of 10% CaCl$_2$-2H$_2$0 per liter. The trace metals solution was composed of 13.9 g of FeSO$_4$-7H$_2$O, 8.5 g of MnSO$_4$-H$_2$O, 14.28 g of ZnSO$_4$-7H$_2$O, 1.63 g of CuSO$_4$, 0.24 g of NiCl$_2$-6H$_2$O, and 3.0 g of citric acid per liter. Hemin was added to a final concentration of 0.01 mg/ml from a fresh 10 mg/ml stock prepared in 50 mM NaOH. The shake flasks were incubated at 34° C. and 200 rpm for 7 to 8 days. The best peroxidase producer was designated JRoC50.3.18A.

Example 7

Transformation of *Aspergillus oryzae* JRoC50.3.18A with pAJ023

*Aspergillus oryzae* strain JRoC50.3.18A was transformed with pAJ023 in order to determine whether overexpression of the *Aspergillus oryzae* hemB gene increased peroxidase production. As a control, pBANe6 was also used to transform *Aspergillus oryzae* JRoc 50.3.18A.

The transformation was conducted with protoplasts at a concentration of 2×10$^7$ protoplasts per ml. One hundred µl of protoplasts were incubated on ice with 10 µg DNA and 200 µl of 60% PEG 4000-10 mM HEPES-10 mM CaCl$_2$ solution for 30 minutes. One ml of SPTC (40% PEG 4000, 0.8 M sorbitol, 0.05 M Tris pH 8.0, 0.05 M CaCl$_2$) was added and the protoplasts were incubated at 34° C. for 20 minutes. Aliquots of 0.25 ml of the transformation were added to 15 ml of COVE agar overlay (same as COVE media+0.7% low melt agar) prior to plating onto COVE transformation plates (per liter: 0.52 g of KCl, 0.52 g of MgSO$_4$-7H$_2$O, 1.52 g of KH$_2$PO$_4$, 1 ml of trace metals solution as described in Example 6, 342.3 g of sucrose, 25 g of Noble agar, 10 ml of 1 M acetamide, and 10 ml of 3 M CsCl) for amdS transformations. Plates were incubated 5–7 days at room temperature. Transformants were transferred to plates of the same medium and incubated 3–5 days at 37° C. The transformants were then purified by streaking spores and picking isolated colonies using the same plates under the same conditions.

Example 8

Peroxidase production by hemB primary transformants

A total of 20 *Aspergillus oryzae* hemB transformants and 42 control transformants (transformants of JRoC 50.3.18A with the *Aspergillus oryzae* expression vector without *Aspergillus oryzae* hemB) were grown in 24 well plates and assayed for peroxidase production as described in Example 6.

The results of the peroxidase assays showed no increase in the number of transformants producing higher levels of peroxidase activity relative to the control transformants.

DEPOSIT OF MICROORGANISMS

The following strain has been deposited according to the Budapest Treaty in the Agricultural Research Service Patent Culture Collection (NRRL), Northern Regional Research Laboratory, 1815 University Street, Peoria, Ill. 61604, USA.

| Strain | Accession Number | Deposit Date |
|---|---|---|
| *E. coli* DH5α (pAJ007-6) | NRRL B-21564 | April 22, 1996 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of each deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. An isolated nucleic acid sequence encoding a porphobilinogen synthase, wherein the nucleic acid sequence (a) encodes a porphobilinogen synthase having an amino acid sequence which has at least 90% identity with amino acids 1 to 375 of SEQ ID NO:2, or (b) hybridizes under high stringency conditions with nucleotides 383 to 1553 of SEQ ID NO:1, or the cDNA sequence contained in nucleotides 383 to 1553 of SEQ ID NO:1.

2. The nucleic acid sequence of claim 1, wherein the nucleic acid sequence encodes a porphobilinogen synthase with an amino acid sequence having at least 90% identity with amino acids 1 to 375 of SEQ ID NO:2.

3. The nucleic acid sequence of claim 2, wherein the nucleic acid sequence encodes a porphobilinogen synthase with an amino acid sequence having at least 95% identity with amino acids 1 to 375 of SEQ ID NO:2.

4. The nucleic acid sequence of claim 1, wherein the nucleic acid sequence comprises SEQ ID NO:1.

5. The nucleic acid sequence of claim 4, wherein the nucleic acid sequence comprises nucleotides 383 to 1553 of SEQ ID NO:1.

6. The nucleic acid sequence of claim 5, which encodes amino acids 1 to 375 of SEQ ID NO:2.

7. The nucleic acid sequence of claim 1, which hybridizes under high stringency conditions with nucleotides 383 to 1553 of SEQ ID NO:1, or the cDNA sequence contained in nucleotides 383 to 1553 of SEQ ID NO:1.

8. The nucleic acid sequence of claim 1, wherein the nucleic acid sequence is obtained from *Aspergillus oryzae*.

9. The nucleic acid sequence of claim 8, wherein the nucleic acid sequence is obtained from *Aspergillus oryzae* IFO 4177.

10. The nucleic acid sequence of claim 1, which is contained in the plasmid pAJ007-6 which is contained in *Escherichia coli* NRRL B-21564.

11. A nucleic acid construct comprising the nucleic acid sequence of claim 1 operably linked to regulatory regions capable of directing the expression of the porphobilinogen synthase in a suitable expression host.

12. A recombinant vector comprising a nucleic acid construct of claim 11.

13. A recombinant host cell comprising the nucleic acid construct of claim 11.

14. The recombinant host cell of claim 13, which is a bacterial cell.

15. The recombinant host cell of claim 13, which is a fungal cell.

16. The recombinant host cell of claim 15, wherein the fungal cell is a filamentous fungal cell.

17. The recombinant host cell of claim 16, wherein the filamentous fungal cell is an Acremonium, Aspergillus, Fusarium, Humicola, Myceliophthora, Mucor, Neurospora, Penicillium, Thielavia, Tolypocladium, or Trichoderma cell.

18. The recombinant host cell of claim 16, wherein the filamentous fungal cell is a Fusarium cell.

19. The recombinant host cell of claim 16, wherein the filamentous fungal cell is an Aspergillus cell.

20. The recombinant host cell of claim 15, wherein the fungal cell is a yeast cell.

21. The recombinant host cell of claim 20, wherein the yeast cell is a Saccharomyces or Schizosaccharomyces cell.

22. The recombinant host cell of claim 13, wherein the nucleic acid construct is integrated into the host cell genome.

23. A method for producing a porphobilinogen synthase comprising (a) cultivating an Aspergillus strain comprising the nucleic acid sequence of claim 1 to produce the porphobilinogen synthase; and (b) recovering the porphobilinogen synthase.

24. A method for producing a porphobilinogen synthase comprising (a) cultivating the host cell of claim 13 comprising a nucleic acid construct comprising a nucleic acid sequence encoding the porphobilinogen synthase under conditions conducive to expression of the porphobilinogen synthase; and (b) recovering the porphobilinogen synthase.

* * * * *